United States Patent [19]

Bang et al.

[11] Patent Number: 5,196,322

[45] Date of Patent: Mar. 23, 1993

[54] VECTORS AND COMPOUNDS FOR EXPRESSION OF ZYMOGEN FORMS OF HUMAN PROTEIN C

[75] Inventors: Nils U. Bang; Hartmut Ehrlich; Brian W. Grinnell; S. Betty Yan, all of Indianapolis, Ind.

[73] Assignee: Eli Lilly and Company, Indianapolis, Ind.

[21] Appl. No.: 771,880

[22] Filed: Oct. 4, 1991

Related U.S. Application Data

[63] Continuation of Ser. No. 512,620, Apr. 11, 1990, abandoned, which is a continuation of Ser. No. 138,009, Dec. 28, 1987, abandoned.

[51] Int. Cl.$^5$ .................. C12N 9/64; C12N 15/06; C12N 15/79; C12N 15/52
[52] U.S. Cl. .................. 435/69.8; 435/172.3; 435/226; 435/240.25; 435/320.1; 536/23.5; 935/14; 935/27; 935/34; 935/48
[58] Field of Search .................. 435/69.1, 69.6, 172.1, 435/172.3, 240.2, 320.1, 226, 69.8; 536/27; 935/32, 48, 70

[56] References Cited

U.S. PATENT DOCUMENTS 4,775,624 10/1988 Bang et al. .................. 435/226

FOREIGN PATENT DOCUMENTS 0191606 8/1986 European Pat. Off. .
0215548 3/1987 European Pat. Off. .
0245949 11/1987 European Pat. Off. .

OTHER PUBLICATIONS

Norris et al., Nucleic Acids Research, vol. #15, pp. 5103-5107 (1983).
Chang, J. "Thrombin Specificity," *Eur. J. Biochem.,* 151: 217-224 (1985).
Marsh et al., 1983, Biochemistry 22:4170.
Endres et al., 1975, Arch. Bioch. Biophy. 168:180.
Chang, 1985, Eur. J. Biochem. 151:217.
Fenton, 1981, Ann. N.Y. Acad. Sci. 370:468.

*Primary Examiner*—Robert A. Wax
*Assistant Examiner*—Dian C. Jacobson
*Attorney, Agent, or Firm*—Douglas K. Norman; Leroy Whitaker

[57] ABSTRACT

A method for the recombinant production of zymogen forms of human protein C is described. These zymogen forms differ from native zymogen protein C in their increased sensitivity to activation by thrombin and thrombin/thrombomodulin. DNA compounds, vectors, and transformants useful in the method are also disclosed.

20 Claims, 5 Drawing Sheets

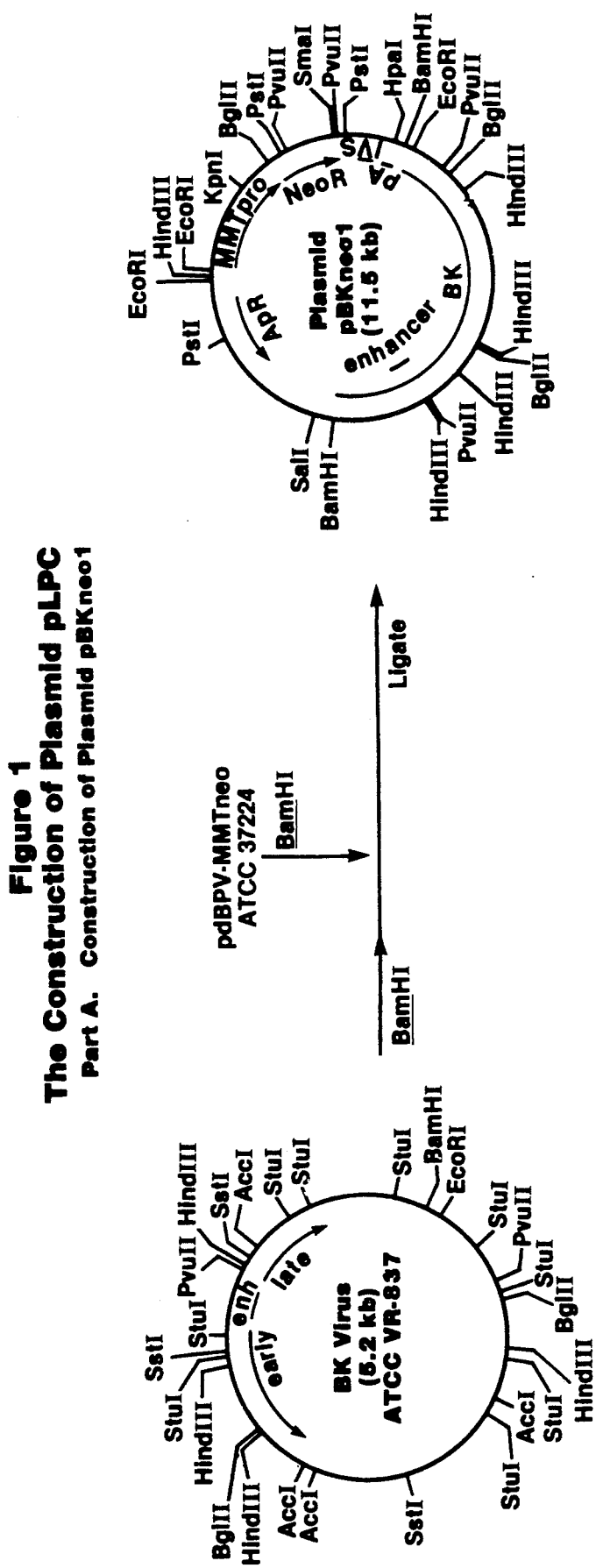

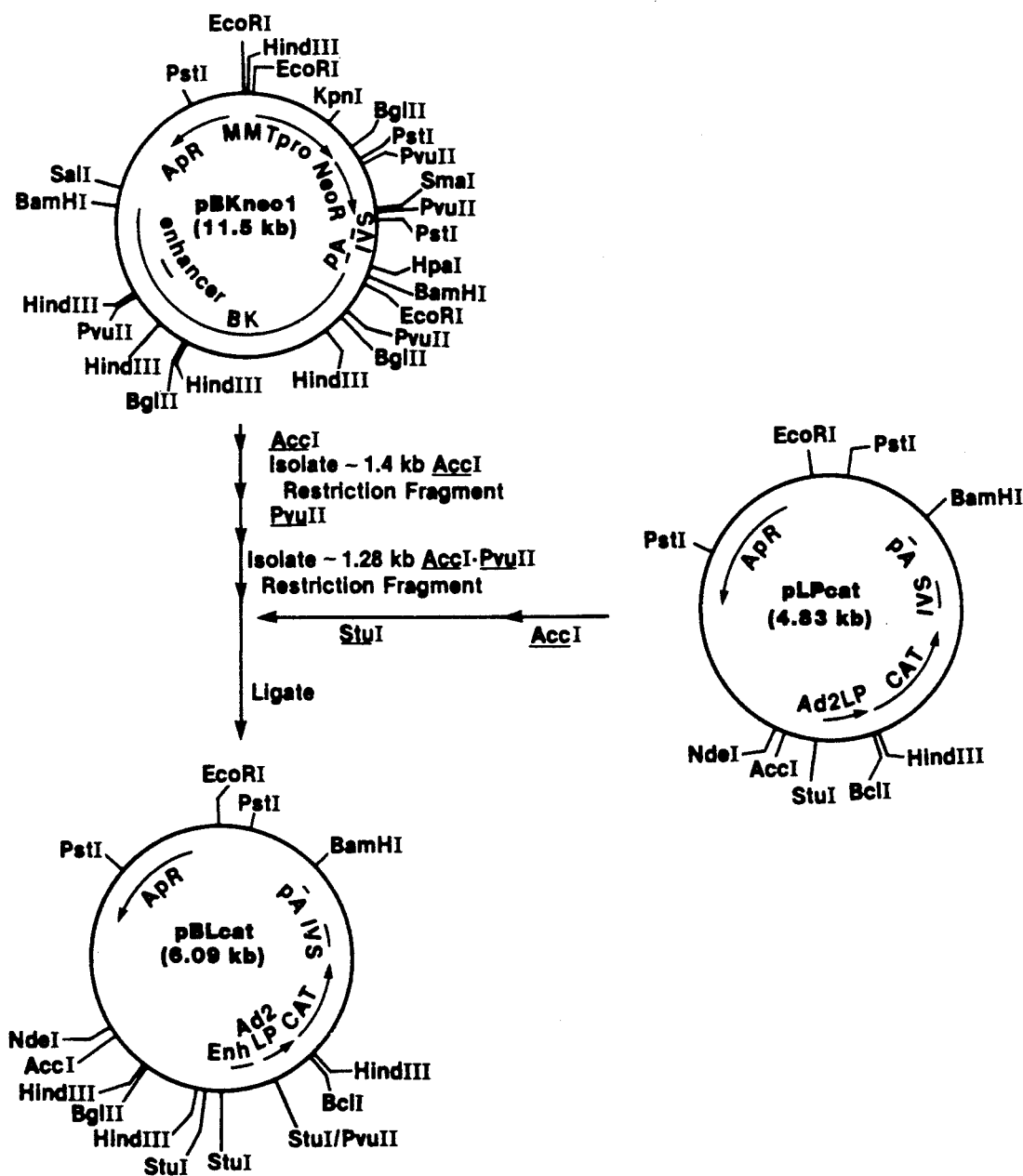

The Construction of Plasmid pLPC
Part D. Final Construction of Plasmid pLPC

Construction of Plasmid pL133

VECTORS AND COMPOUNDS FOR EXPRESSION OF ZYMOGEN FORMS OF HUMAN PROTEIN C

This application is a continuation of application Ser. No. 07/512,620, filed on Apr. 11, 1990, now abandoned, which is a continuation of application Ser. No. 07/138,009, filed on Dec. 28, 1987, now abandoned.

SUMMARY OF THE INVENTION

The present invention provides novel DNA compounds and recombinant DNA cloning vectors that encode novel zymogen forms of human protein C. These zymogens can be activated in vivo by thrombin alone at a rate of clinical significance and are much more susceptible to activation by thrombin/thrombomodulin than native protein C zymogen. The expression vectors provide a simple and efficient means for expressing these human protein C zymogens in recombinant host cells. Native human protein C zymogens require treatment with high levels of thrombin, or thrombin and thrombomodulin, or other expensive enzymes for activation. The present invention provides a method for producing zymogen forms of human protein C that serve as much better substrates for thrombin and consequently can be activated in the presence of lower levels of thrombin, or thrombin/thrombomodulin, or other enzymes. Most importantly, the zymogen forms of human protein C of the invention can be activated by thrombin even in the presence of physiological $Ca^{2+}$, which is inhibitory to the activation of native protein C zymogen by thrombin. The novel zymogen forms of human protein C differ from those known in the art in the amino acid residue sequence of the activation peptide, which is removed from the zymogen forms to produce activated human protein C. These novel zymogen forms of protein C offer special advantages in the treatment of blood disorders involving coagulation.

BACKGROUND OF THE INVENTION

The Role of Protein C in the Regulation of Blood Coagulation

Protein C, a vitamin K dependent plasma protein, is of major physiological importance in the control of hemostasis. Protein C is synthesized as an inactive molecule, herein called nascent protein C. Nascent protein C undergoes complex processing, giving rise to a number of different inactive molecules as is more fully described below. Inactive, secreted forms of protein C are referred to herein as zymogen protein C. Activation of protein C occurs in the blood by a reaction involving a thrombomodulin-thrombin complex. Activated protein C, together with its cofactor protein S, is an anticoagulant of important physiological significance. Activated protein C can prevent intravascular thrombosis and control the extension of existing clots. The mechanism of action of the activated form of protein C and the mechanism of activation of the inactive zymogen into the active protease have been clarified in recent years (for review, see J. E. Gardiner and J. H. Griffin, *Progress in Hematology*, Vol. XIII, pp. 265-278, ed. Elmer B. Brown, Grune and Stratton, Inc., 1983).

The activation of protein C involves thrombin, the final serine protease in the coagulation cascade, and an endothelial cell membrane-associated glycoprotein called thrombomodulin. Thrombomodulin forms a tight, stoichiometric complex with thrombin. Thrombomodulin, when complexed with thrombin, totally changes the functional properties of thrombin. Thrombin normally clots fibrinogen, activates platelets, and converts clotting cofactors V and VIII to their activated forms, Va and VIIIa. Finally, thrombin activates protein C, but only very slowly and inefficiently, and the activation is further inhibited by physiological $Ca^{2+}$. In contrast, thrombin complexed with thrombomodulin does not clot fibrinogen, activate platelets, or convert clotting factors V and VIII to their activated counterparts Va and VIIIa, but does become a very efficient activator of protein C zymogen in the presence of physiological $Ca^{2+}$. The rate constant of protein C zymogen activation by thrombomodulin-thrombin is over 1,000 fold higher than the rate constant for thrombin alone.

To understand how activated protein C down-regulates blood coagulation, the following brief description of the coagulation enzyme system is provided. The coagulation system is best looked at as a chain reaction involving the sequential activation of zymogens into active serine proteases. This chain reaction eventually produces the enzyme thrombin, which through limited proteolysis converts plasma fibrinogen into the insoluble gel fibrin. Two key events in the coagulation cascade are the conversion of clotting factor X to Xa by clotting factor IXa and the conversion of prothrombin into thrombin by clotting factor Xa. Both of these reactions occur on cell surfaces, most notably the platelet surface, and both reactions require cofactors. The major cofactors, factors V and VIII, in the system circulate as relatively inactive precursors, but when the first few molecules of thrombin are formed, thrombin loops back and activates the cofactors through limited proteolysis. The activated cofactors, Va and VIIIa, accelerate both the conversion of prothrombin into thrombin and also the conversion of factor X to factor Xa by approximately five orders of magnitude. Activated protein C preferentially acts on, to proteolytically degrade, hydrolyze, and irreversibly destroy clotting cofactors Va and VIIIa, the activated forms of the inactive clotting factors V and VIII. Clotting factors V and VIII, in contrast, are very poor substrates for activated protein C in vivo.

An important cofactor for activated protein C is protein S, another vitamin K-dependent plasma protein. Protein S substantially increases activated protein C-mediated hydrolysis of factors Va and VIIIa 25 fold.

Protein C as a Therapeutic Agent

Protein C is recognized as a valuable therapeutic agent (see, for example, European Patent Publications Nos. 0215548 and 0191606, incorporated herein by reference). Activated protein C is a novel antithrombotic agent with a wider therapeutic index than available anticoagulants, such as heparin and the oral hydroxycoumarin type anticoagulants. Neither zymogen protein C nor activated protein C is effective until thrombin is generated, because thrombin is needed to convert clotting factors V to Va and VIII to VIIIa; the activated forms of these two cofactors are the preferred substrate for activated protein C. Thrombin is also required to activate zymogen protein C, for without the thrombomodulin-thrombin complex, the protein C zymogen is not converted into its active counterpart.

Activated protein C is an on-demand anticoagulant, because activated protein C works by inactivating cofactors Va and VIIIa. Because thrombin is required to convert factors V and VIII to their activated counterparts Va and VIIIa, protein C only acts as an anticoagulant after thrombin is generated. Conventional anticoagulants, in contrast to activated protein C, maintain a constant anticoagulant state throughout the circulation for as long as they are given to the patient, thereby substantially increasing the risk of bleeding complications over that for protein C or activated protein C. Activated protein C is therefore an on-demand anticoagulant of wide clinical utility for use as an alternative to heparin and the hydroxycoumarins.

In some disease states, such as hereditary protein C deficiency, protein C zymogen is of great therapeutic importance. In congenital homozygous protein C deficiency, affected individuals die in early childhood from purpura fulminans, an often lethal form of disseminated intravascular coagulation. In heterozygous protein C deficiency, affected individuals suffer severe, recurrent thromboembolic episodes. It is well established clinically that plasma protein concentrates designed to treat hemophilia B or factor IX deficiency, which contain protein C as an impurity, are effective in the prevention and treatment of intravascular clotting in heterozygous protein C deficiency. Protein C levels have also been noted to be abnormally low in thrombotic states such as disseminated intravascular coagulation and in disease states predisposing to thrombosis, such as major trauma, major surgery, and cancer.

The Synthesis and Activation of Human Protein C

To facilitate an understanding of the activation of protein C and the invention, the coding sequence, and corresponding amino acid residue sequence, for nascent human protein C is depicted below. This amino acid residue sequence, and relevant portions thereof, also characterizes "native human protein C" for purposes of the present invention.

```
              10           20            30           40
5'-ATG TCG CAG CTC ACA AGC CTC CTG CTG TTC GTG GCC ACC TGG GGA ATT
H2N—MET TRP GLN LEU THR SER LEU LEU LEU PHE VAL ALA THR TRP GLY ILE
                 5                    10                  15

50           60           70           80           90
   TCC GGC ACA CCA GCT CCT CTT GAC TCA GTG TTC TCC AGC AGC GAG CGT
   SER GLY THR PRO ALA PRO LEU ASP SER VAL PHE SER SER SER GLU ARG
              20                  25                  30

100          110          120          130          140
   GCC CAC CAG GTG CTG CGG ATC CGC AAA CGT GCC AAC TCC TTC CTG GAG
   ALA HIS GLN VAL LEU ARG ILE ARG LYS ARG ALA ASN SER PHE LUE GLU
              35                  40                  45

150          160          170          180          190
   GAG CTC CGT CAC AGC AGC CTG GAG CGG GAG TGC ATA GAG GAG ATC TGT
   GLU LEU ARG HIS SER SER LEU GLU ARG GLU CYS ILE GLU GLU ILE CYS
       50                  55                  60

200          210          220          230          240
   GAC TTC GAG GAG GCC AAG GAA ATT TTC CAA AAT GTG GAT GAC ACA CTG
   ASP PHE GLU GLU ALA LYS GLU ILE PHE GLN ASN VAL ASP ASP THR LEU
   65                  70                  75                  80

250          260          270          280
   GCC TTC TGG TCC AAG CAC GTC GAC GGT GAC CAG TGC TTG GTC TTG CCC
   ALA PHE TRP SER LYS HIS VAL ASP GLY ASP GLN CYS LEU VAL LEU PRO
              85                  90                  95

290          300          310          320          330
   TTG GAG CAC CCG TGC GCC AGC CTG TGC TGC GGG CAC GGC ACG TCG ATC
   LEU GLU HIS PRO CYS ALA SER LEU CYS CYS GLY HIS GLY THR CYS ILE
              100                 105                 110

340          350          360          370          380
   GAC GGC ATC GGC AGC TTC AGC TGC GAC TGC CGC AGC GGC TGG GAG GGC
   ASP GLY ILE GLY SER PHE SER CYS ASP CYS ARG SER GLY TRP GLU GLY
              115                 120                 125

390          400          410          420          430
   CGC TTC TGC CAG CGC GAG GTG AGC TTC CTC AAT TGC TCG CTG GAC AAC
   ARG PHE CYS GLN ARG GLU VAL SER PHE LEU ASN CYS SER LEU ASP ASN
              130                 135                 140

440          450          460          470          480
   GGC GGC TGC ACG CAT TAC TGC CTA GAG GAG GTG GGC TGG CGG CGC TGT
   GLY GLY CYS THR HIS TYR CYS LEU GLU GLU VAL GLY TRP ARG ARG CYS
   145                 150                 155                 160

490          500          510          520
   AGC TGT GCG CCT GGC TAC AAG CTG GGG GAC GAC CTC CTG CAG TGT CAC
   SER CYS ALA PRO GLY TYR LYS LEU GLY ASP ASP LEU LEU GLN CYS HIS
              165                 170                 175

530          540          550          560          570
   CCC GCA GTG AAG TTC CCT TGT GGG AGG CCC TGG AAG CGG ATG GAG AAG
   PRO ALA VAL LYS PHE PRO CYS GLY ARG PRO TRP LYS ARG MET GLU LYS
              180                 185                 190
```

```
        580              590              600              610              620
AAG CGC AGT CAC CTG AAA CGA GAC ACA GAA GAC CAA GAA GAC CAA GTA
LYS ARG SER HIS LEU LYS ARG ASP THR GLU ASP GLN GLU ASP GLN VAL
                195                       200                      205

630              640              650              660              670
GAT CCG CGG CTC ATT GAT GGG AAG ATG ACC AGG CGG GGA GAC AGC CCC
ASP PRO ARG LEU ILE ASP GLY LYS MET THR ARG ARG GLY ASP SER PRO
            210                      215                      220

680              690              700              710              720
TGG CAG GTG GTC CTG CTG GAC TCA AAG AAG AAG CTG GCC TGC GGG GCA
TRP GLN VAL VAL LEU LEU ASP SER LYS LYS LYS LEU ALA CYS GLY ALA
225                      230                      235                      240

730              740              750              760
GTG CTC ATC CAC CCC TCC TGG GTG CTG ACA GCG GCC CAC TGC ATG GAT
VAL LEU ILE HIS PRO SER TRP VAL LEU THR ALA ALA HIS CYS MET ASP
                    245                      250                      255

770              780              790              800              810
GAG TCC AAG AAG CTC CTT GTC AGG CTT GGA GAG TAT GAC CTG CGG CGC
GLU SER LYS LYS LEU LEU VAL ARG LEU GLY GLU TYR ASP LEU ARG ARG
                260                      265                      270

820              830              840              850              860
TGG GAG AAG TGG GAG CTG GAC CTG GAC ATC AAG GAG GTC TTC GTC CAC
TRP GLU LYS TRP GLU LEU ASP LEU ASP ILE LYS GLU VAL PHE VAL HIS
            275                      280                      285

870              880              890              900              910
CCC AAC TAC AGC AAG AGC ACC ACC GAC AAT GAC ATC GCA CTG CTG CAC
PRO ASN TYR SER LYS SER THR THR ASP ASN ASP ILE ALA LEU LEU HIS
            290                      295                      300

920              930              940              950              960
CTG GCC CAG CCC GCC ACC CTC TCG CAG ACC ATA GTG CCC ATC TGC CTC
LEU ALA GLN PRO ALA THR LEU SER GLN THR ILE VAL PRO ILE CYS LEU
305                      310                      315                      320

970              980              990              1000
CCG GAC AGC GGC CTT GCA GAG CGC GAG CTC AAT CAG GCC GGC CAG GAG
PRO ASP SER GLY LEU ALA GLU ARG GLU LEU ASN GLN ALA GLY GLN GLU
                    325                      330                      335

1010             1020             1030             1040             1050
ACC CTC GTG ACG GGC TGG GGC TAC CAC AGC AGC CGA GAG AAG GAG GCC
THR LEU VAL THR GLY TRP GLY TYR HIS SER SER ARG GLU LYS GLU ALA
                340                      345                      350

1060             1070             1080             1090             1100
AAG AGA AAC CGC ACC TTC GTC CTC AAC TTC ATC AAG ATT CCC GTG GTC
LYS ARG ASN ARG THR PHE VAL LEU ASN PHE ILE LYS ILE PRO VAL VAL
            355                      360                      365

1110             1120             1130             1140             1150
CCG CAC AAT GAG TGC AGC GAG GTC ATG AGC AAC ATG GTG TCT GAG AAC
PRO HIS ASN GLU CYS SER GLU VAL MET SER ASN MET VAL SER GLU ASN
            370                      375                      380

1160             1170             1180             1190             1200
ATG CTG TGT GCG GGC ATC CTC GGG GAC CGG CAG GAT GCC TGC GAG GGC
MET LEU CYS ALA GLY ILE LEU GLY ASP ARG GLN ASP ALA CYS GLU GLY
385                      390                      395                      400

1210             1220             1230             1240
GAC AGT GGG GGG CCC ATG GTC GCC TCC TTC CAC GGC ACC TGG TTC CTG
ASP SER GLY GLY PRO MET VAL ALA SER PHE HIS GLY THR TRP PHE LEU
                405                      410                      415

1250             1260             1270             1280             1290
GTG GGC CTG GTG AGC TGG GGT GAG GGC TGT GGG CTC CTT CAC AAC TAC
VAL GLY LEU VAL SER TRP GLY GLU GLY CYS GLY LEU LEU HIS ASN TYR
                420                      425                      430

1300             1310             1320             1330             1340
GGC GTT TAC ACC AAA GTC AGC CGC TAC CTC GAC TGG ATC CAT GGG CAC
GLY VAL TYR THR LYS VAL SER ARG TYR LEU ASP TRP ILE HIS GLY HIS
            435                      440                      445
```

-continued

```
    1350            1360            1370            1380
ATC AGA GAC AAG GAA GCC CCC CAG AAG AGC TGG GCA CCT TAG-3'
ILE ARG ASP LYS GLU ALA PRO GLN LYS SER TRP ALA PRO—COOH
            450             455             460
``` wherein A is deoxyadenyl, G is deoxyguanyl, C is deoxycytidyl, T is thymidyl, ALA is Alanine, ARG is Arginine, ASN is Asparagine, ASP is Aspartic acid, —COOH is the carboxy terminus, CYS is Cysteine, GLN is Glutamine, GLU is Glutamic Acid, GLY is Glycine, HIS is Histidine, H₂N- is the amino terminus, ILE is Isoleucine, LEU is Leucine, LYS is Lysine, MET is Methionine, PHE is Phenylalanine, PRO is Proline, SER is Serine, THR is Threonine, TRP is Tryptophan, TYR is Tyrosine, and VAL is Valine.

The DNA sequence depicted above was derived from cDNA clones prepared from human liver mRNA that encodes human protein C. Those skilled in the art recognize that the degenerate nature of the genetic code enables one to construct many different DNA sequences that encode the same amino acid residue sequence. The cDNA sequence for nascent human protein C depicted above is thus only one of many possible nascent human protein C-encoding sequences. In constructing the cDNA clones, a 5' poly G sequence, a 3' poly C sequence, and both 5' and 3' PstI restriction enzyme recognition sequences were constructed at the ends of the protein C-encoding cDNA. Two of these cDNA clones were manipulated to construct a DNA molecule comprising both the coding sequence of nascent human protein C and also portions of the DNA encoding the untranslated mRNA at the 5' and 3' ends of the coding region. This DNA molecule was inserted into the PstI site of plasmid pBR322 to construct plasmid pHC7. Plasmid pHC7 thus comprises the coding sequence above and, again depicting only one strand of the molecule, also contains these additional sequences:

```
5'-C TGC AGG GGG GGG GGG GGG GGG GGG CTG TCA TGG CGG CAG GAC
    GGC GAA CTT GCA GTA TCT CCA CGA CCC GCC CCT ACA GGT GCC
    AGT GCC TCC AGA-3'
``` and

```
5'-CGA CCC TCC CTG CAG GGC TGG GCT TTT GCA TGG CAA TGG ATG GGA
    CAT TAA AGG GAC ATG TAA CAA GCA CAC CCC CCC CCC CCC CCC
    CCC CCC CCT GCA G-3'
``` at the 5' and 3' ends, respectively, of the coding strand of the nascent human protein C coding sequence. Due to the complementary nature of DNA base-pairing, the sequence of one strand of a double-stranded DNA molecule is sufficient to determine the sequence of the opposing strand. Plasmid pHC7 can be conventionally isolated from E. coli K12 RR1/pHC7, a strain deposited with and made part of the permanent stock culture collection of the Northern Regional Research Laboratory (NRRL), Peoria, Ill. A culture of E. coli K12 RR1/pHC7 can be obtained from the NRRL under the accession number NRRL B-15926. A restriction site and function map of plasmid pHC7 is presented in FIG. 2 of the accompanying drawings.

Nascent protein C can also be depicted schematically, as shown below.

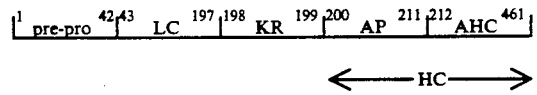

pre-pro—amino acid residues 1-42 of nascent human protein C encode the signal peptide and propeptide of human protein C, important for directing secretion and γ-carboxylation of protein C.

LC—amino acid residues 43-197 of nascent protein C, once post-translationally modified, constitute the light chain (LC) of both the two-chain zymogen (formed from one-chain zymogen by removal of the KR dipeptide, as discussed below) and activated forms of protein C.

KR—amino acid residues 198-199 of nascent human protein C; these residues are believed to be removed (on the basis of homology with bovine protein C), probably by a two-step process comprising a first cleavage (either between residues 197-198 or 199-200) followed by carboxypeptidase or aminopeptidase action, to form two-chain protein C.

AP—amino acid residues 200-211 of nascent protein C constitute the activation peptide, which is removed from the zymogen forms of protein C to obtain activated protein C.

AHC—amino acid residues 212-461 of nascent protein C, once post-translationally modified, constitute the activated heavy chain (AHC) of active protein C.

HC—the heavy chain of the two chain form of protein C zymogen, once post-translationally modified, is composed of amino acid residues 200-461, the AP and AHC.

Human protein C zymogen is a serine protease precursor synthesized in the liver and present in the blood. For expression of complete biological activity, protein C requires post-translational modifications for which vitamin K is needed. The two-chain, disulfide-linked, protein C zymogen arises from the single-chain zymogen by limited proteolysis. This limited proteolysis is believed to include cleavage and removal of amino acid residues 198 and 199. The activation of the two-chain zymogen into the active serine protease involves the proteolytic cleavage of an ARG-LEU peptide bond (residues 211 and 212). This latter cleavage releases a dodecapeptide (residues 200-211), the activation peptide, that constitutes the amino-terminus of the larger (heavy) chain of the two-chain zymogen molecule. Protein C is significantly glycosylated; the mature enzyme contains ~23% carbohydrate. Protein C also contains a number of unusual amino acids, including γ-carboxyglutamic acid and β-hydroxyaspartic acid (erythro-L-β-hydroxy aspartate). γ-carboxyglutamic acid (gla) is produced by γ-glutamyl carboxylation from glutamic acid residues with the aid of a hepatic microsomal carboxylase which requires vitamin K as a cofactor.

The activation of human protein C can also be represented schematically and is shown below. Those skilled in the art recognize that the order of the steps shown in the schematic do not necessarily reflect the order of the steps in the in vivo pathway.

```
                    pre-pro-LC—KR—AP—AHC        nascent protein C
post-translational modification,        |
i.e., γ-carboxylation of specific       |
glutamic acid residues, β-              |
hydroxylation of an aspartic            |
acid residue, and glycosylation         ▼ secretion, the removal of               |
residues 1-42, which may                |
involve more than one                   |
proteolytic cleavage                    ▼

LC—KR—AP—AHC        one-chain zymogen
removal of residues 198-199,            |
about 90% of the zymogen                |
protein C found in human blood          |
is the two chain form (S—S=             |
disulfide bond)                         ▼

LC           two-chain zymogen
                           |
                          S—S
                           |
                         AHC—AP
activation by                           |
thrombin-thrombomodulin                 |
                                        ▼

LC           activated protein C
                           |
                          S—S
                           |
                          AHC
```

The present invention provides novel compounds, vectors, transformants, and methods for the recombinant expression of novel protein C zymogens.

DEFINITIONS

For purposes of the present invention, as disclosed and claimed herein, the following terms are as defined below.

Ad2LP—the major late promoter of adenovirus type 2.

Amino acid residues in proteins or peptides described herein as abbreviated as follows:

| Three-Letter Abbreviation | Amino Acid Residue | One-Letter Abbreviation |
|---|---|---|
| PHE | Phenylalanine | F |
| LEU | Leucine | L |
| ILE | Isoleucine | I |
| MET | Methionine | M |
| VAL | Valine | V |
| SER | Serine | S |
| PRO | Proline | P |
| THR | Threonine | T |
| ALA | Alanine | A |
| TYR | Tyrosine | Y |
| HIS | Histidine | H |
| GLN | Glutamine | Q |
| ASN | Asparagine | N |
| LYS | Lysine | K |
| ASP | Aspartic Acid | D |
| GLU | Glutamic Acid | E |
| CYS | Cysteine | C |
| TRP | Tryptophan | W |
| ARG | Arginine | R |
| GLY | Glycine | G |

ApR—the ampicillin-resistant phenotype or gene conferring same.

BK—DNA from BK virus.

CAT—the chloramphenicol acetyltransferase gene.

Enh or enhancer—the enhancer of BK virus.

ep or SV40ep—a DNA segment comprising the SV40 early promoter of the T-antigen gene, the T-antigen binding sites, the SV40 enhancer, and the SV40 origin of replication.

γ-carboxylation—a reaction which adds a carboxyl group to glutamic acids at the γ-carbon.

γ-carboxylated protein—a protein in which some glutamic acids residues have undergone γ-carboxylation.

IVS—DNA encoding an intron, also called an intervening sequence.

MMTpro—the promoter of the mouse metallothionein-I gene.

Nascent protein—the polypeptide produced upon translation of a mRNA transcript, prior to any post-translational modifications. However, post-translational modifications such as γ-carboxylation of glutamic acid residues and hydroxylation of aspartic acid residues may occur before a protein is fully translated from an mRNA transcript.

NeoR—a neomycin resistance-conferring gene, which can also be used to confer resistance to the antibiotic G418.

pA—a DNA sequence encoding a polyadenylation signal.

Promoter—a DNA sequence that directs transcription of DNA into RNA.

Protein C activity—any property of human protein C responsible for proteolytic, amidolytic, esterolytic, and biological (anticoagulant or profibrinolytic) activities. Methods for testing for protein anticoagulant activity are well known in the art, i.e., see Grinnell et al., 1987, Biotechnology 5:1189.

Recombinant DNA Cloning Vector—any agent, including, but not limited to; chromosomally integrating agents, autonomously replicating plasmids, and phages, comprising a DNA molecule to which one or more additional DNA segments can be or have been added.

Recombinant DNA Expression Vector—any recombinant DNA cloning vector into which a promoter has been incorporated and positioned to drive expression of a gene product.

Recombinant DNA Vector—any recombinant DNA cloning or expression vector.

Replicon—A DNA sequence that controls and allows for autonomous replication of a plasmid or other vector.

Restriction Fragment—any linear DNA sequence generated by the action of one or more restriction endonuclease enzymes.

Sensitive Host Cell—a host cell that cannot grow in the presence of a given antibiotic or other toxic compound without a DNA segment that confers resistance thereto.

TcR—the tetracycline-resistant phenotype or gene conferring same.

Transformation—the introduction of DNA into a recipient host cell that changes the genotype of the recipient cell.

Transformant—a recipient host cell that has undergone transformation.

Translational Activating Sequence—any DNA sequence, inclusive of that encoding a ribosome binding site and translational start codon, such as 5'-ATG-3', that provides for the translation of a mRNA transcript into a peptide or polypeptide.

Zymogen—an enzymatically inactive precursor of a proteolytic enzyme. Protein C zymogen, as used herein, refers to secreted, inactive forms, whether one chain or two chain, of protein C.

BRIEF DESCRIPTION OF THE FIGURES

FIG. 1, Part A depicts the construction of plasmid pBKneol from BK virus and plasmid pdBPV-MMtneo.

FIG. 1, Part B depicts the construction of plasmid pLPcat from adenovirus 2 and plasmid pSV2cat.

FIG. 1, Part C depicts the construction of plasmid pBLcat from plasmid pBKneol and plasmid pLPcat.

FIG. 1, Part D depicts the construction of plasmid pLPC from plasmid pBLcat and plasmid pL133.

DETAILED DESCRIPTION OF THE INVENTION

Figure 1:
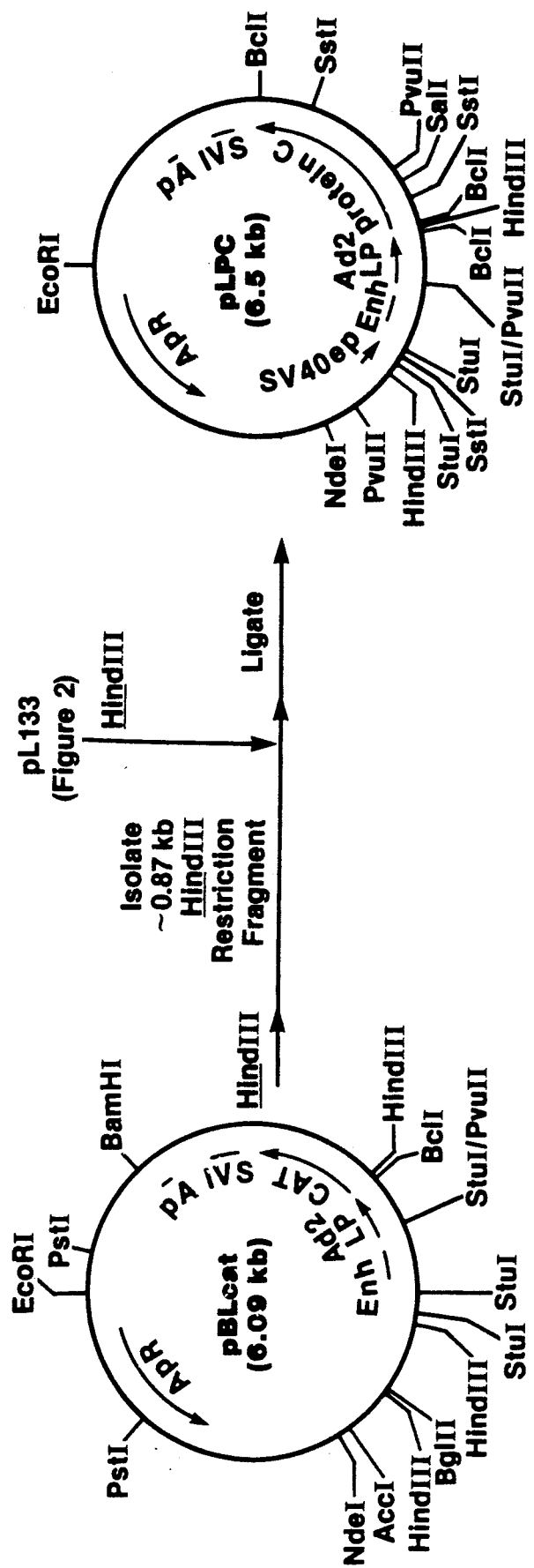
FIG. 1 consists of four parts and schematically illustrates the construction protocol for plasmid pLPC, a starting material used in the construction of starting plasmid pLAPC.

The present invention provides DNA compounds that code for the expression of novel zymogen forms of human protein C. Several methods of producing native human protein C zymogen and nascent human protein C have been described (see European Patent Publications 215548 and 191606). These prior art methods provide for the expression of zymogen forms of human protein C that do not differ from the zymogen forms present in human blood. The protein C zymogen produced by these methods must be treated with substances such as α-thrombin, trypsin, or a mixture of thrombin and thrombomodulin (whether in vivo or in vitro) to obtain activated protein C. In addition, a zymogen form of human protein C produced by recombinant DNA technology that is identical to zymogen forms of human protein C found naturally in human blood will only be activated in the body by the natural activation pathway involving the thrombin-thrombomodulin complex. Native human protein C zymogen can be activated by thrombin alone; however, the activation requires the absence of $Ca^{2+}$ and such high levels of thrombin and/or protein C zymogen that it is not a significant in vivo pathway to activated protein C.

The present invention provides zymogen forms of human protein C that can be activated in vivo by thrombin alone at a rate of clinical significance. In addition, these zymogen forms are much more susceptible to activation by thrombin/thrombomodulin than native human protein C zymogen. The present invention also provides DNA compounds, recombinant DNA expression vectors, transformed cell lines, and methods for the recombinant expression of these novel zymogen forms of human protein C. The method for producing these zymogen forms of human protein C comprises:

(A) transforming a eukaryotic host cell with a recombinant DNA vector, said vector comprising:
    (i) a DNA sequence that encodes an amino acid residue sequence, said amino residue sequence comprising, from the amino terminus to the carboxy terminus:
        a) a signal peptide and pro-peptide of a γ-carboxylated, secreted protein;
        b) the light chain of human protein C;
        c) a dipeptide selected from the group consisting of LYS-ARG, ARG-LYS, LYS-LYS, and ARG-ARG; and
        d) the amino acid residue sequence:

| | | | | | | | ASP | THR | GLU | ASP | GLN | GLU | ASP | GLN | VAL |
|---|---|---|---|---|---|---|---|---|---|---|---|---|---|---|---|
| $R_1$ | $R_2$ | ARG | LEU | ILE | $R_3$ | GLY | LYS | MET | THR | ARG | ARG | GLY | ASP | SER | PRO |
| TRP | GLN | VAL | VAL | LEU | LEU | ASP | SER | LYS | LYS | LYS | LEU | ALA | CYS | GLY | ALA |
| VAL | LEU | ILE | HIS | PRO | SER | TRP | VAL | LEU | THR | ALA | ALA | HIS | CYS | MET | ASP |
| GLU | SER | LYS | LYS | LEU | LEU | VAL | ARG | LEU | GLY | GLU | TYR | ASP | LEU | ARG | ARG |
| TRP | GLU | LYS | TRP | GLU | LEU | ASP | LEU | ASP | ILE | LYS | GLU | VAL | PHE | VAL | HIS |
| PRO | ASN | TYR | SER | LYS | SER | THR | THR | ASP | ASN | ASP | ILE | ALA | LEU | LEU | HIS |
| LEU | ALA | GLN | PRO | ALA | THR | LEU | SER | GLN | THR | ILE | VAL | PRO | ILE | CYS | LEU |
| PRO | ASP | SER | GLY | LEU | ALA | GLU | ARG | GLU | LEU | ASN | GLN | ALA | GLY | GLN | GLU |
| THR | LEU | VAL | THR | GLY | TRP | GLY | TYR | HIS | SER | SER | ARG | GLU | LYS | GLU | ALA |
| LYS | ARG | ASN | ARG | THR | PHE | VAL | LEU | ASN | PHE | ILE | LYS | ILE | PRO | VAL | VAL |
| PRO | HIS | ASN | GLU | CYS | SER | GLU | VAL | MET | SER | ASN | MET | VAL | SER | GLU | ASN |
| MET | LEU | CYS | ALA | GLY | ILE | LEU | GLY | ASP | ARG | GLN | ASP | ALA | CYS | GLU | GLY |
| ASP | SER | GLY | GLY | PRO | MET | VAL | ALA | SER | PHE | HIS | GLY | THR | TRP | PHE | LEU |

-continued

| VAL | GLY | LEU | VAL | SER | TRP | GLY | GLU | GLY | CYS | GLY | LEU | LEU | HIS | ASN | TYR |
|---|---|---|---|---|---|---|---|---|---|---|---|---|---|---|---|
| GLY | VAL | TYR | THR | LYS | VAL | SER | ARG | TYR | LEU | ASP | TRP | ILE | HIS | GLY | HIS |
| ILE | ARG | ASP | LYS | GLU | ALA | PRO | GLN | LYS | SER | TRP | ALA | PRO—COOH | | | | wherein $R_1$ is selected from the group consisting of PHE, GLY, TYR, and TRP, $R_2$ is selected from the group consisting of VAL and PRO, $R_3$ is selected from the group consisting of ASP and ASN, ARG is Arginine, ASN is Asparagine, ASP is Aspartic acid, —COOH is the carboxy terminus, CYS is Cysteine, GLN is Glutamine, GLU is Glutamic Acid, GLY is Glycine, HIS is Histidine, ILE is Isoleucine, LEU is Leucine, LYS is Lysine, MET is Methionine, PHE is Phenylalanine, PRO is Proline, SER is Serine, THR is Threonine, TRP is Tryptophan, TYR is Tyrosine, and VAL is Valine; and (ii) a promoter positioned to drive expression of said DNA sequence; and (B) culturing said host cell transformed in step (A) under conditions that allow for expression of said DNA sequence. This method and compounds useful in the method are more fully described below.

The invention also provides DNA compounds for use in the method of producing these novel zymogen forms of human protein C. These novel compounds all encode a pre-propeptide comprising a signal peptide for directing secretion and a propeptide from a γ-carboxylated (through the action of a vitamin K-dependent carboxylase) protein. Such propeptide sequences are well-known in the art. See, for example, Suttie et al., 1987, Proc. Natl. Acad. Sci. 84:634-637. Preferably, and for ease of construction, both the signal peptide coding sequence and the propeptide coding sequence will be derived from the amino acid residue sequence of the pre-propeptide of a γ-carboxylated protein. Examples of such γ-carboxylated proteins include, but are not limited to, factor VII, factor IX, factor X, prothrombin, protein S, protein Z, and, protein C. A DNA sequence encoding the pre-propeptide of human protein C is most preferred for use in the vectors of the invention.

The DNA compounds of the invention further comprise the coding sequence for the light chain of human protein C positioned immediately adjacent to, downstream of, and in translational reading frame with the pre-propeptide coding sequence. The light chain of human protein C contains amino acid residues 43 to 197, inclusive, of nascent protein C, as depicted in the background section above. The amino-terminal portions of the vitamin K-dependent plasma proteins, such as the amino-terminal portion of the light chain of protein C, are responsible for calcium-binding activity of these proteins. The calcium-binding domains of these plasma proteins, such as factor VII, factor IX, factor X, prothrombin, and protein S, are interchangeable (see European Patent Publication No. 0215548A1, at pages 12 and 13) and equivalent to the calcium-binding domain of the light chain of human protein C.

The DNA compounds of the invention further comprise the coding sequence for the dipeptide LYS-ARG (KR) positioned immediately adjacent to, downstream of, and in translational reading frame with the light chain coding sequence. A dibasic dipeptide such as LYS-ARG is positioned in the nascent protein at the carboxyl-terminal side of the light chain. The orientation of the LYS-ARG dipeptide in the expressed protein is irrelevant for purposes of the present invention. Dibasic dipeptides such as LYS-LYS or ARG-ARG are equivalent to the LYS-ARG dipeptide for purposes of the present invention. For purposes of the present invention, however, the dipeptide LYS-ARG, which is the dipeptide in native human protein C, is preferred.

Immediately downstream of the codons for the LYS-ARG dipeptide is the coding sequence of the activation peptide. In the compounds of the invention, changes in the activation peptide coding sequence (and corresponding amino acid sequence) are primarily responsible for the property of increased thrombin-sensitivity of these novel zymogens.

Those skilled in the art will recognize that the zymogen forms of the present invention primarily differ from native zymogen forms of human protein C as described below. In native human protein C the activation peptide is:

200 201 202 203 204 205 206 207 208 209 210 211
ASP—THR—GLU—ASP—GLN—GLU—ASP—GLN—VAL—ASP—PRO—ARG, in which the numbers refer to the position of the amino acid residues in nascent human protein C. The present invention discloses that changing the ASP residue at position 209 to either a PHE, GLY, TYR, or TRP residue will result in the corresponding zymogen form having a greater sensitivity to cleavage by thrombin alone, in addition to a greater sensitivity to cleavage by the thrombin-thrombomodulin complex.

Other amino acid substitutions, in conjunction with the substitutions at position 209, can also enhance the thrombin-sensitivity of the resulting zymogen. The phrase "resulting zymogen" is used to indicate that although substitutions are described with reference to amino acid positions in nascent human protein C, nascent human protein C must first be secreted (resulting in removal of amino acid residues 1 through 42) to obtain a zymogen form. Substitution of the proline residue (in the activation peptide) at position 210 in nascent human protein C, in addition to one of the four substitutions at position 209 described above, for a valine residue thus results in a novel zymogen of the present invention. Substitution of the aspartic acid residue (in the activated heavy chain) at position 214 in nascent human protein C, in addition to one of the four substitutions at position 209 described above, and whether or not in addition to the substitution at position 210 described above, for an asparagine residue also results in a novel zymogen of the present invention.

Thus, the preferred novel zymogen forms of human protein C of the present invention result from secretion and processing of nascent human protein C molecules with the amino acid residue sequence depicted below:

| | | | | | | | | | | | | | | |
|---|---|---|---|---|---|---|---|---|---|---|---|---|---|---|
| H₂N-MET | TRP | GLN | LEU | THR | SER | LEU | LEU | PHE | VAL | ALA | THR | TRP | GLY | ILE |
| SER | GLY | THR | PRO | ALA | PRO | LEU | ASP | SER | PHE | ALA | SER | SER | GLU | ARG |
| ALA | HIS | GLN | VAL | LEU | ARG | ILE | ARG | LYS | ALA | ASN | SER | PHE | LEU | GLU |
| GLU | LEU | ARG | HIS | GLU | SER | LEU | GLU | GLU | CYS | ILE | GLU | GLU | ILE | CYS |
| ASP | PHE | GLU | GLU | SER | LYS | GLU | ILE | GLN | ASN | VAL | ASP | VAL | THR | LEU |
| ALA | PHE | TRP | PRO | ALA | HIS | PHE | ASP | ASP | GLY | HIS | LEU | VAL | LEU | PRO |
| LEU | GLU | HIS | SER | LYS | ALA | GLY | LEU | CYS | GLN | GLY | GLY | THR | CYS | ILE |
| ASP | GLY | ILE | GLY | SER | PHE | CYS | CYS | ARG | GLY | SER | GLY | TRP | GLU | GLY |
| ARG | PHE | CYS | GLN | ARG | GLU | ASP | PHE | CYS | ASN | SER | LEU | ARG | ASP | ASN |
| GLY | GLY | CYS | THR | HIS | TYR | PHE | GLU | VAL | VAL | CYS | TRP | ARG | CYS | CYS |
| SER | CYS | ALA | PRO | GLY | TYR | GLY | GLY | LEU | ASP | GLY | LEU | LEU | GLN | HIS |
| PRO | ALA | VAL | LYS | PHE | PRO | GLY | ARG | PRO | TRP | LYS | ARG | MET | GLU | LYS |
| LYS | ARG | SER | HIS | LEU | LYS | ARG | ASP | THR | ASP | GLN | GLU | ASP | GLN | VAL |
| R₁ | R₂ | ARG | LEU | ILE | R₃ | GLY | LYS | ARG | THR | ARG | GLY | SER | SER | PRO |
| TRP | GLN | VAL | VAL | LEU | LEU | ASP | SER | LYS | LYS | LEU | ALA | CYS | GLY | ALA |
| VAL | LEU | ILE | HIS | PRO | SER | TRP | VAL | ALA | THR | LEU | HIS | CYS | MET | ASP |
| GLU | SER | LYS | HIS | PRO | LEU | VAL | ARG | ALA | ALA | LEU | ASP | LEU | ARG | ARG |
| TRP | GLU | LEU | LYS | GLU | GLU | ASP | LEU | GLU | GLU | VAL | TYR | PHR | VAL | HIS |
| PRO | ASN | SER | TRP | LYS | ASP | ASP | ASP | ILE | LYS | ILE | ALA | LEU | LEU | HIS |
| LEU | ALA | GLN | SER | THR | GLN | THR | ILE | VAL | ASN | VAL | PRO | ILE | CYS | LEU |
| PRO | ASP | PRO | GLY | ALA | ARG | GLU | ASN | ASN | ASP | SER | ALA | GLY | GLY | GLU |
| THR | LEU | THR | GLY | TRP | TYR | LEU | SER | SER | PHE | ILE | GLU | LYS | MET | ALA |
| LYS | ARG | ASN | THR | PHE | LEU | ARG | TYR | LEU | ARG | PHE | ILE | PRO | ARG | ASP |
| PRO | HIS | ASN | ARG | SER | ASN | GLU | LEU | ALA | LYS | SER | ASN | SER | VAL | ARG |
| MET | LEU | CYS | GLU | ILE | MET | ASP | ASP | GLY | GLU | ARG | MET | CYS | GLN | HIS |
| ASP | SER | GLY | PRO | MET | TRP | SER | ARG | ALA | HIS | PHE | ASP | THR | GLU | HIS |
| VAL | GLY | LEU | GLY | TRP | VAL | TYR | LEU | GLU | GLY | CYS | LEU | LEU | PHE | LEU |
| GLY | VAL | TYR | THR | VAL | ALA | ARG | ARG | ARG | LYS | ASP | TRP | HIS | ASN | TYR |
| ILE | ARG | ASP | LYS | GLU | ALA | GLN | LYS | GLU | GLU | TRP | ALA | PRO-COOH | | | wherein $R_1$ is PHE, GLY, TYR, or TRP; $R_2$ is PRO or VAL; and $R_3$ is ASP or ASN.

Those skilled in the art will recognize that, due to the degeneracy of the genetic code, a variety of DNA compounds can encode the polypeptide depicted above. Consequently, the constructions described below and in the accompanying Examples for the preferred DNA compounds, vectors, and transformants of the invention are merely illustrative and do not limit the scope of the invention.

The novel coding sequences of the invention can be readily constructed starting from a coding sequence for nascent human protein C from which the AP-encoding region has been deleted by site-specific mutagenesis. Shown schematically, this coding sequence has the structure:

| pre-pro | LC | KR | AHC |

As described in the accompanying examples, this coding sequence was inserted into a recombinant DNA expression vector and the resulting vector was designated plasmid pLAPC. Plasmid pLAPC serves as useful starting material for the construction of illustrative vectors of the invention that drive high-level recombinant expression of the novel zymogen forms of human protein C of the invention. The construction protocol for plasmid pLAPC from starting plasmid pHC7 is described in Example 1.

Plasmid pHC7 is available from the Northern Regional Research Center (NRRL), Peoria, Ill. 61604 in *E. coli* K12 RR1/pHC7 under the accession number NRRL B-15926.

Plasmid pLPC-167G is an illustrative expression vector of the invention in which the codon for aspartic acid at position 209 in nascent human protein C has been changed to a codon for glycine. The construction protocol for plasmid pLPC-167G is described in detail in Example 3. Essentially, the construction involved site-specific mutagenesis of the protein C coding sequence. A portion of the protein C coding sequence comprising the activation peptide-encoding DNA was isolated from plasmid pHC7, inserted into phage M13mp18, and then altered by site-specific mutagenesis. The mutagenized coding sequence was then cloned into a eukaryotic cloning vector to achieve a plasmid, designated pLPC-167G, identical to plasmid pLAPC, except for the insertion of a coding sequence for the activation peptide in which the codon for glycine has been substituted for the codon for aspartic acid at position 209.

Plasmid pLPC-167F is an illustrative expression vector of the invention in which the codon for aspartic acid at position 209 in nascent human protein C has been changed to a codon for phenylalanine. The construction protocol for plasmid pLPC-167F is described in detail in Example 4. Other than the different mutagenizing oligonucleotide used in the construction, the construction protocol for plasmid pLPC-167F was substantially the same as the construction protocol for plasmid pLPC-167G.

The methods of site-specific mutagenesis described in the accompanying Examples are illustrative and can be used to generate other compounds and vectors of the invention. As stated above, these other compounds of the invention include the nascent proteins produced upon translation of the mRNA transcripts generated from the DNA coding sequences of the invention. The compounds of the invention also include the zymogen forms generated upon secretion of the nascent proteins of the invention. In addition, in the case of the compounds of the invention in which the aspartic acid residue at position 214 has been changed to an asparagine residue, the activated protein C derivative produced upon activation of the zymogen form is also a compound of the invention. Thus, the compounds of the invention include DNA coding sequences, expression vectors that drive expression of those sequences, nascent proteins produced upon translation of mRNA transcripts generated from those coding sequences, zymogens produced upon secretion of those nascent proteins, and activated derivatives of certain of the zymogens.

In the preferred coding sequences of the invention (and thus the preferred nascent proteins, zymogens, and activated molecules), the coding sequence encodes an amino acid residue sequence identical to that of nascent human protein C except for the substitutions at positions 209, 210, and 214. These substitutions are depicted below in Table I.

TABLE I

Amino Acid Residues Encoded at Positions 209, 210, and 214 in the Preferred Coding Sequences of the Invention

| Compound | 209 | 210 | 214 |
|---|---|---|---|
| 1 | PHE | PRO | ASP |
| 2 | PHE | PRO | ASN |
| 3 | PHE | VAL | ASP |
| 4 | PHE | VAL | ASN |
| 5 | GLY | PRO | ASP |
| 6 | GLY | PRO | ASN |
| 7 | GLY | VAL | ASP |
| 8 | GLY | VAL | ASN |
| 9 | TYR | PRO | ASP |
| 10 | TYR | PRO | ASN |
| 11 | TYR | VAL | ASP |
| 12 | TYR | VAL | ASN |
| 13 | TRP | PRO | ASP |
| 14 | TRP | PRO | ASN |
| 15 | TRP | VAL | ASP |
| 16 | TRP | VAL | ASN |

The DNA compounds of the invention can also be synthesized chemically, or by combining restriction fragments, or by a combination of techniques known in the art. DNA synthesizing machines are also available and can be used to construct the compounds of the invention.

The illustrative vectors of the invention, plasmids pLPC-167G and pLPC-167F, comprise the BK enhancer positioned to stimulate transcription by the adenovirus major late promoter of the coding sequence of the invention. Those skilled in the art recognize that a great number of eukaryotic promoters, enhancers, and expression vectors are known in the art and can be used in the method of the present invention. Those skilled in the art also recognize that a eukaryotic expression vector can function without an enhancer element. The key aspect of the present invention does not reside in the particular enhancer, if any, or promoter, used to drive expression of the protein C zymogen but rather resides in the novel coding sequence and corresponding proteins produced from that sequence.

However, choice of vector elements, such as promoters, enhancers, and selectable markers, can have great impact on the ultimate levels of protein produced by a eukaryotic host cell. U.S. patent application Ser. No. 849,999, filed Apr. 9, 1986, incorporated herein by reference, discloses a number of expression vectors for native zymogen protein C that utilize the BK enhancer to stimulate a eukaryotic promoter positioned to drive expression of nascent human protein C. These vectors drive especially high expression levels when transformed into eukaryotic cells that also express an immediate-early gene product of a large DNA virus, such as the E1A gene product of adenovirus. As is evident from the illustrative vectors pLPC-167G and pLPC-167F disclosed herein, the BK enhancer-E1A gene product expression method of Ser. No. 849,999 is especially preferred for use with the vectors of the present invention.

The present invention is not limited to use in a particular eukaryotic host cell. A variety of eukaryotic host cells are available from depositories such as the American Type Culture Collection (ATCC) Rockville, Md. 20852, and are suitable for use with the vectors of the invention. The choice of a particular host cell depends to some extent on the particular expression vector used to drive expression of the protein C-encoding DNA cell lines with illustrative vectors pLPC-167G and pLPC-167F.

The vectors of the invention can be transformed into and expressed in a variety of eukaryotic, especially mammalian, host cells. Vectors of the invention that possess no selectable marker with which to isolate and identify stable eukaryotic transformants are useful not only for purposes of transient assay but also for purposes of cotransformation, a procedure disclosed in U.S. Pat. No. 4,399,216, issued Aug. 26, 1983, and incorporated herein by reference. The vectors of the invention can also comprise sequences that allow for replication in *E. coli*, as it is usually more efficient to prepare plasmid DNA in *E. coli* than in other host organisms.

Expression of the coding sequences for human protein C contained on the vectors of the invention occurs in those host cells in which the particular promoter associated with the structural gene functions. Exemplary host cells suitable for use in the invention are listed in Table II, along with appropriate comments.

TABLE II

| Host Cell | Origin | Source | Comments |
|---|---|---|---|
| HepG-2 | Human Liver Hepatoblastoma | *ATCC #HB 8065 | U.S. Pat. No. 4,393,133 describes the use of this cell line. |
| CV-1 | African Green Monkey Kidney | ATCC #CCL 70 | |
| LLC-MK$_2$ original | Rhesus Monkey Kidney | ATCC #CCL 7 | |
| LLC-MK$_2$ derivative | Rhesus Monkey Kidney | ATCC #CCL 7.1 | Grows faster than ATCC #CCL 7 |
| 3T3 | Mouse Embryo Fibroblasts | ATCC #CCL 92 | |
| CHO-K1 | Chinese Hamster Ovary | ATCC #CCL 61 | Proline-requiring. Derivatives of CHO-K1, such as the dhfr-derivative DXB11, can be generated from this host. |
| HeLa | Human Cervix Epitheloid | ATCC #CCL 2 | |
| RPMI8226 | Human Myeloma | ATCC #CCL 155 | IgG lambda-type light chain secreting |
| H4IIEC3 | Rat Hepatoma | ATCC #CRL 1600 | Derivatives, such as 8-azaguanine-resistant FAZA host cells, can be generated from this host. |
| C127I | Mouse Fibroblast | ATCC #CRL 1616 | |
| HS-Sultan | Human Plasma Cell Plasmocytoma | ATCC #CRL 1484 | |
| BHK-21 | Baby Hamster Kidney | ATCC #CCL 10 | |

*American Type Culture Collection, 12301 Parklawn Drive, Rockville, Maryland 20852-1776 compounds of the invention. Because nascent human protein C and the nascent human protein C derivatives of the invention undergo substantial post-translational modification, however, some host cells are more preferred for use with the vectors of the invention. U.S. patent application Ser. No. 849,999 and Grinnell et al., 1987, Bio/Technology 5:1189 disclose that adenovirus-transformed, human embryonic kidney cells are especially preferred for use in the recombinant production of γ-carboxylated proteins such as human protein C. One such adenovirus-transformed, human embryonic kidney cell line is the 293 cell line, available from the ATCC under the accession number ATCC CRL 1573. The 293 cell line is also preferred for use with the vectors of the present invention.

However, the advantages of producing a γ-carboxylated protein, such as human protein C zymogen, in an adenovirus-transformed cell line are not limited to adenovirus-transformed human embryonic kidney cells. In fact, adenovirus-transformed cells in general are exceptional hosts for the production of γ-carboxylated human protein C. One especially preferred cell line of this type is the AV12-664 (hereinafter "AV12") cell line, available from the ATCC under the accession number ATCC CRL 9595. The AV12 cell line was constructed by injecting a Syrian hamster in the scruff of the neck with human adenovirus 12 and isolating cells from the resulting tumor. Example 5, below, describes the transformation of both the 293 and AV12

As indicated by Table II, many mammalian host cells possess the necessary cellular machinery for the recognition and proper processing of the signal peptide on the nascent proteins of the invention and provide the post-translational modifications, such as glycosylation, γ-carboxylation, and β-hydroxylation, as are observed in human protein C present in blood plasma. A wide variety of vectors, discussed below, exists for the transformation of such eukaryotic host cells, but the specific vectors exemplified below are in no way intended to limit the scope of the present invention.

The pSV2-type vectors comprise segments of the SV40 genome that constitute a defined eukaryotic transcription unit-promoter (ep), intervening sequence (IVS), and polyadenylation (pA) site. In the absence of SV40 T-antigen, the plasmid pSV2-type vectors transform mammalian and other eukaryotic host cells by integrating into the host cell chromosomal DNA. A variety of plasmid pSV2-type vectors have been constructed (see *Eukaryotic Viral Vectors*, edited by Gluzman, published by Cold Spring Harbor Laboratories, Cold Spring Harbor, N.Y., 1982), such as plasmids pSV2-gpt, pSV2-neo, pSV2-dhfr, pSV2-hyg, and pSV2-β-globin, in which the SV40 promoter drives transcription of an inserted gene. These vectors are suitable for use with the coding sequences of the invention and are available either from the American Type Culture Collection (ATCC) in Rockville, Md. or from the Northern Regional Research Laboratory (NRRL) in Peoria, Ill.

Plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification, described in a review article by Schimke, 1984, Cell 37:705-713, can involve DNA sequences closely contiguous with the dhfr gene, such as a nascent human protein C-encoding sequence of the invention, and thus can be used to increase production of the protein C zymogens of the invention.

Plasmids which were constructed for expression of the nascent protein C and protein C zymogens of the invention in mammalian and other eukaryotic host cells can utilize a wide variety of promoters. The present invention is in no way limited to the use of the particular eukaryotic promoters exemplified herein. Promoters such as the SV40 late promoter or the eukaryotic promoters disclosed in Bucher et al., 1986, Nuc. Acids Res. 14(24):1009, or promoters from eukaryotic genes, such as, for example, the estrogen-inducible chicken ovalbumin gene, the interferon genes, the glucocorticoid-inducible tyrosine aminotransferase gene, the thymidine kinase gene, and the major early and late adenovirus genes, can be readily isolated and modified for use on recombinant DNA expression vectors designed to produce human protein C zymogen in eukaryotic host cells. Eukaryotic promoters can also be used in tandem to drive expression of a coding sequence of the invention. Furthermore, a large number of retroviruses are known that infect a wide range of eukaryotic host cells. The long terminal repeats in the retrovirus DNA often encode promoter activity and thus can be used to drive expression of the coding sequences of the invention.

Plasmid pRSVcat (ATCC 37152) comprises portions of the long terminal repeat of the Rous Sarcoma virus (RSV), a virus known to infect chicken and other host cells. The RSV long terminal repeat sequences can be isolated on an ~0.76 kb NdeI-HindIII restriction fragment of plasmid pRSVcat. The promoter in the RSV long terminal repeat (Gorman et al., 1982, P.N.A.S. 79:6777) is suitable for use in vectors of the invention. Plasmid pMSVi (NRRL B-15929) comprises the long terminal repeats of the Murine Sarcoma virus (MSV), a virus known to infect mouse and other host cells. These repeat sequences are suitable for use as a promoter in the vectors of the invention. The mouse metallothionein (MMT) promoter has also been well characterized for use in eukaryotic host cells and is suitable for use in the vectors of the invention. The MMT promoter is present in the 15 kb plasmid pdBPV-MMTneo (ATCC 37224), which can serve as the starting material for the construction of other plasmids of the present invention.

Many modifications and variations of the present illustrative DNA sequences and plasmids are possible. For example, the degeneracy of the genetic code allows for the substitution of nucleotides throughout polypeptide coding regions, as well as in the translational stop signal, without alteration of the encoded polypeptide coding sequence. Such substitutable sequences can be deduced from the known amino acid or DNA sequence of human protein C and can be constructed by following conventional synthetic or site specific mutagenesis procedures. Synthetic methods can be carried out in substantial accordance with the procedures of Itakura et al., 1977 Science 198:1056 and Crea et al., 1978, Proc. Nat. Acad. Sci. USA 75:5765. Therefore, the present invention is in no way limited to the DNA sequences and plasmids specifically exemplified.

After transformation of a vector of the invention into a eukaryotic host cell, one can select transformants on the basis of a selectable phenotype. This selectable phenotype can be conferred either by a selectable marker present on the expression vector or present on another vector cotransformed with the expression vector into the host cell. Once transformants are selected, it is desirable to identify which transformants are expressing the highest levels of the desired protein encoded on the expression vector. Such identification is especially important after a cotransformation procedure, which generates a number of transformants that contain only the plasmid containing the selectable marker and so do not contain the expression vector. In Example 6, below, a protocol not only for identifying cells that express and secrete a desired protein but also for quantifying, relative to the other cells examined using the method, the amount of protein secreted is described. The protocol also allows for the isolation of viable cells secreting the highest levels of a desired protein.

Activated protein C has substantial antithrombotic properties in the prevention of extension of intravenous thrombi, in the prevention of formation of arterial thrombi, and in the prevention of death and organ failure from Gram negative sepsis, endotoxemia, and disseminated intravascular coagulation. In animal experiments, infusion of native zymogen protein C was without effect in the treatment of Gram negative septicemia with shock and disseminated intravascular coagulation (DIC). These negative results indicated that in this form of widespread microvascular thrombosis involving massive thrombin generation, insufficient thrombomodulin was present to complex with thrombin and activate the infused zymogen.

The major disadvantage of activated protein C, as with any activated serine protease, is its short half-life ($T\frac{1}{2}$) as compared to the zymogen precursor. The $T\frac{1}{2}$ in dogs was established to be 11 minutes and the $T\frac{1}{2}$ in monkeys to be 22 to 26 minutes. In comparison, the $T\frac{1}{2}$ of native protein C zymogen in man is estimated at 6 hours. The reason for the shorter biological half lives of activated serine proteases, including activated protein C, as compared to their zymogens, are complex and involve both cellular and humoral mechanisms. Activated serine proteases also form complexes with serine protease inhibitors normally present in plasma. Activated protein C (APC) complexes with a newly described APC inhibitor as well as with alpha-2 macroglobulin. The inactive zymogens, including the protein C zymogens of the invention, do not react with serine protease inhibitors.

The advantage of the protein C zymogens of this invention is that they are better activated by thrombin than native protein C zymogen, because thrombin no longer has an absolute requirement for complexing with thrombomodulin to activate these zymogens in the presence of $Ca^{2+}$. It follows that these protein C zymogens, when administered, can be activated at sites of intravascular thrombin generation, i.e., at any site where an intravascular thrombus is under developement. Thus, these recombinant protein C zymogens can be used as pro drugs and will become activated only at the sites of thrombin generation. Because these thrombin-sensitive zymogens can be administered in the zymogen form, they will not complex with protein C inhibitors and will exhibit a biological half-life equal to that of native protein C zymogen.

The recombinant protein C zymogens of the invention are useful in the prevention and treatment of a wide variety of acquired disease states involving intravascular coagulation, including deep vein thrombosis, pulmonary embolism, peripheral arterial thrombosis, emboli originating from the heart or peripheral arteries, acute myocardial infarction, thrombotic strokes, and disseminated intravascular coagulation. These protein C derivatives can also be used efficiently in the treatment of the significant numbers of patients with heterozygous protein C deficiencies presenting recurrent deep vein thrombosis and in the case of the homozygous protein C deficient patients with purpura fulminans.

Experimental and clinical data suggest that conventional anticoagulants, particularly warfarin, are useful in the treatment of invasive cancers and act to prevent or reduce the distant metastatic lesions of these malignancies. In addition, it is well established that inflammatory stimuli, such as endotoxins, tumor necrosis factor, and interleukin 1, deplete thrombomodulin from the surface of endothelial cells, which is thought to trigger microvascular and macrovascular thrombosis. The recombinant protein C zymogens of the invention represent an attractive alternative to conventional anticoagulants in these clinical situations.

The doses of the protein C zymogens of the invention, because of their prolonged $T_{\frac{1}{2}}$, can be substantially reduced in clinical situations, as compared to activated protein C. In homozygous protein C deficiency, the dose of a protein C zymogen of the invention will range from about 5 mg to 100 mg per treatment, and in heterozygous protein C deficiency, the dose will range from about 2.5 mg to 50 mg per treatment.

An attractive therapeutic indication for activated protein C is in the prevention of deep vein thrombosis and pulmonary embolism, currently treated with low doses of heparin. In high risk patients, particularly patients undergoing surgery, the dose of recombinant activated protein C for prevention of deep vein thrombosis is in the range from 1–10 mg/day. The dose of a protein C zymogen of the invention will range from about 0.25 to 5 mg per day. The added advantage of these zymogens is that they may be given as bolus injections rather than constant IV infusions. Activated protein C must be given by continuous IV infusion because of the short $T_{\frac{1}{2}}$ of that protein. In established, objectively-documented, deep vein thrombosis and/or pulmonary embolism, the dose of activated protein C ranges from 1–10 mg as a loading dose followed by a continuous infusion in amounts ranging from 3–30 mg/day. The protein C zymogens of the invention, on the other hand, may be given by repeated bolus injection in doses not to exceed about 12 mg per 24 hours.

Similar dosage schedules are applicable for the treatment of peripheral arterial thrombi. There is a lower likelihood of bleeding complications from infusions of the protein C zymogens of the invention. Thus, these zymogens can replace heparin intra- and post-surgically in conjunction with thrombectomies or embolectomies, surgical procedures which are often necessary to save ischemic limbs from amputation in the setting of an acute arterial obstruction. Because of their long $T_{\frac{1}{2}}$, as compared to activated protein C, and their relative ease of administration, these zymogens are better suited than activated protein C for the treatment of arterial emboli originating from the heart. The long term administration of these zymogens in doses comparable to those used for the treatment of established deep vein thrombois-pulmonary embolism has substantial utility in the prevention of cardiogenic emboli.

Similarly, the protein C zymogens of the invention can be used for the treatment of emboli originating from thrombi in peripheral arteries, most notably the carotid arteries, which are not treated or prevented satisfactorily with currently used regimens, which include drugs capable of suppressing platelet function, oral anticoagulants, or combinations thereof. As in the case of cardiogenic emboli, these zymogens can be administered long term in the same manner as outlined for cardiogenic emboli and have major potential in the prevention of emboli originating from carotid artery thrombi and resulting in embolic strokes.

The protein C zymogens of the invention are also useful in thrombotic strokes. Today, strokes are not usually treated with conventional anticoagulants. Treatment of strokes with either heparin or oral anticoagulants, although occasionally beneficial, carries a high risk for bleeding into the infarcted brain area, thereby aggravating the neurological deficit accompanying the stroke. Because of their low potential for causing bleeding complications and their selectivity, the zymogens of the invention can be given to stroke victims and can be beneficial in preventing the local extension of the occluding arterial thrombus, thereby reducing the neurological deficit resulting from the stroke. The amount of the zymogen effective in the treatment of stroke will be lower, as compared with activated protein C, but the dose will vary with each patient depending on the nature and severity of the stroke.

The zymogens of the invention will also be useful in treating acute myocardial infarction, because of their pro-fibrinolytic properties, once activated. These zymogens can be given with tissue plasminogen activator during the acute phases of the myocardial infarction. After the occluding coronary thrombus is dissolved, the zymogens can be given for additional days to prevent acute myocardial reinfarction. If activated protein C is administered in this situation, the patient is given a loading dose of 1–10 mg at the time plasminogen activator treatment is initiated followed by a continuous infusion of activated protein C ranging from 3–30 mg/day. In contrast, the zymogens of the invention can be given through bolus injection 3 to 4 times a day in doses not to exceed about 12 mg/day.

Activated protein C is useful in the treatment of disseminated intravascular coagulation. Heparin and the oral anticoagulants have been given to patients with disseminated intravascular coagulation (DIC) in extensive clinical trials, but the results have been disappointing. In disseminated intravascular coagulation, activated protein C, as well as the zymogens of the present invention, has a distinct advantage over conventional anticoagulants. As mentioned above, it has been established in animal experiments that the protein C zymogen is ineffective in the prevention of death and organ damage from Gram negative septicemia and disseminated intravascular coagulation. In contrast, the protein C zymogens of the invention, being highly susceptible to activation by thrombin, will be effective treatment for disseminated intravascular coagulation. The estimated requirements for activated protein C to treat DIC is approximately 100 mg/day; the doses of the zymogen forms of the invention for treatment of DIC are not to exceed about 30 mg/day, administered as repeated bolus injections.

Conventional anticoagulant drugs, particularly warfarin, are useful in the treatment of invasive malignant tumors. Many tumor cells produce substances which trigger the activation of the coagulation system resulting in local fibrin deposits. These fibrin deposits function as "nests" in which cancer cells can divide to form metastatic lesions. However, it is not possible to administer warfarin or other conventional anticoagulants in combination with the more intensive and effective forms of chemotherapy, because such therapy always produces a sharp drop in the platelet count, and thrombocytopenia combined with warfarin therapy puts the patient at an unacceptably high risk for serious bleeding complications. The protein C derivatives of the invention, like activated protein C, being more selective than conventional anticoagulants and having a far higher therapeutic index than either heparin or the oral anticoagulants, can be given relatively safely to the thrombocytopenic patient, thus making possible the treatment of patients with invasive cancers with effective and intensive chemotherapy in combination with a protein C zymogen of the invention. Treatment will follow a dosage regimen comparable to that used in deep vein thrombosis-pulmonary embolism.

The zymogens, and activated counterparts, of the present invention can be formulated according to known methods to prepare pharmaceutically useful compositions, whereby a human protein C zymogen or activated protein C of the invention is combined in admixture with a pharmaceutically acceptable carrier vehicle. Suitable carrier vehicles and their formulation, inclusive of other human proteins, e.g., human serum albumin, are described, for example, in *Remington's Pharmaceutical Sciences* 16th ed., 1980, Mack Publishing Co., edited by Osol et al., which is hereby incorporated by reference. Such compositions will contain an effective amount of a protein C zymogen, or activated counterpart, together with a suitable amount of carrier vehicle to prepare pharmaceutically acceptable compositions suitable for effective administration to the host. The protein C composition can be administered parenterally, or by other methods that ensure its delivery to the bloodstream in an effective form.

It should also be noted that the zymogens of the present invention can be used to prepare activated protein C in vitro. Although recombinant methods for producing activated protein C directly in eukaryotic cells are known, these methods require that the activated protein C remain in the culture media for long periods of time. In addition, the activated protein C must be purified from the culture medium, an expensive, multi-step process. Because activated protein C is relatively unstable, these direct expression methods can yield low amounts of activated protein C. In contrast, the zymogens of the invention can be activated by thrombin alone, even in the presence of $Ca^{2+}$, and thus offer significant advantages over known methods for producing activated protein C.

The following Examples illustrate the methods and describe the construction protocols for representative compounds, vectors and transformants of the invention without limiting the same thereto.

EXAMPLE 1

Construction of Plasmid pLAPC

This Example provides a detailed protocol for the construction of plasmid pLAPC. In brief, Example 1A describes the isolation of a DNA fragment encoding a portion of the protein C molecule, including the activation peptide, from plasmid pHC7. Example 1B describes the cloning of this DNA fragment into phage M13mp18 and the removal of the DNA encoding the activation peptide from the resulting recombinant phage by site specific mutagenesis. Example 1C describes the final steps in the construction of plasmid pLAPC, more specifically, the isolation of the mutagenized fragment and its ligation with two fragments derived from plasmid pLPC to yield plasmid pLAPC. The construction protocol for plasmid pLPC is described in Example 2.

A. Isolation of a DNA Fragment Containing the Coding Sequence for the Activation Peptide of Human Protein C Plasmid pHC7 contains the complete coding sequence for nascent human protein C. One liter of L broth (10 g peptone, 10 g NaCl, and 5 g yeast extract) containing 15 μg/ml tetracycline was inoculated with a culture of *E. coli* K12 RR1/pHC7 (NRRL B-15926) and incubated in an air-shaker incubator at 37° C. until the optical density (O.D.) at 590 nm was ~1 absorbance unit, at which time 150 mg of chloramphenicol were added to the culture. The incubation was continued for about 16 hours; the chloramphenicol addition inhibits protein synthesis, and thus inhibits further cell division, but allows plasmid replication to continue.

The culture was centrifuged in a Sorvall GSA rotor (DuPont Co., Instrument Products, Biomedical Division, Newtown, Conn. 06470) at 6000 rpm for 5 minutes at 4° C. The resulting supernatant was discarded, and the cell pellet was washed in 40 ml of TES buffer (10 mM Tris-HCl, pH=7.5; 10 mM NaCl; and 1 mM EDTA) and then repelleted. The supernatant was again discarded, and the cell pellet was frozen in a dry ice-ethanol bath and then thawed. The thawed cell pellet was resuspended in 10 ml of a 25% sucrose/50 mM EDTA solution. About one ml of a 5 mg/ml lysozyme solution; 3 ml of 0.25M EDTA, pH=8.0; and 100 μl of 10 mg/ml RNAse A were added to the solution, which was then incubated on ice for 15 minutes. Three ml of lysing solution (prepared by mixing 3 ml 10% Triton-X 100; 75 ml 0.25M EDTA, pH=8.0; 15 ml of 1M Tris-HCl, pH=8.0; and 7 ml of water) were added to the lysozyme-treated cells, mixed, and the resulting solution incubated on ice for another 15 minutes. The lysed cells were frozen in a dry ice-ethanol bath and then thawed.

The cellular debris was removed from the solution by centrifugation at 25,000 rpm for 40 minutes in an SW27 rotor (Beckman, 7360 N. Lincoln Ave., Lincolnwood, Ill. 60646). About 30.44 g of CsCl and ~1 ml of a 5 mg/ml ethidium bromide solution were added to the solution, the volume of which was then adjusted to 40 ml. The solution was decanted into a Vti50 ultracentrifuge tube (Beckman). The tube was sealed and then centrifuged in a Vti50 rotor at 42,000 rpm for ~16 hours. The resulting plasmid band, visualized with ultraviolet light, was isolated and then placed in a ti75 tube and rotor (Beckman) and centrifuged at 55,000 rpm for 16 hours. Any necessary volume adjustments were made using TES containing 0.761 g/ml CsCl. The plasmid band was again isolated, the ethidium bromide extracted with salt-saturated isopropanol, and finally diluted 1:3 with TES buffer. Two volumes of ethanol were then added to the solution, and the resulting mixture was incubated overnight at −20° C. The plasmid DNA was pelleted by centrifuging the solution in an SS34 rotor (DuPont Co.) for 15 minutes at 10,000 rpm.

Figure 2:
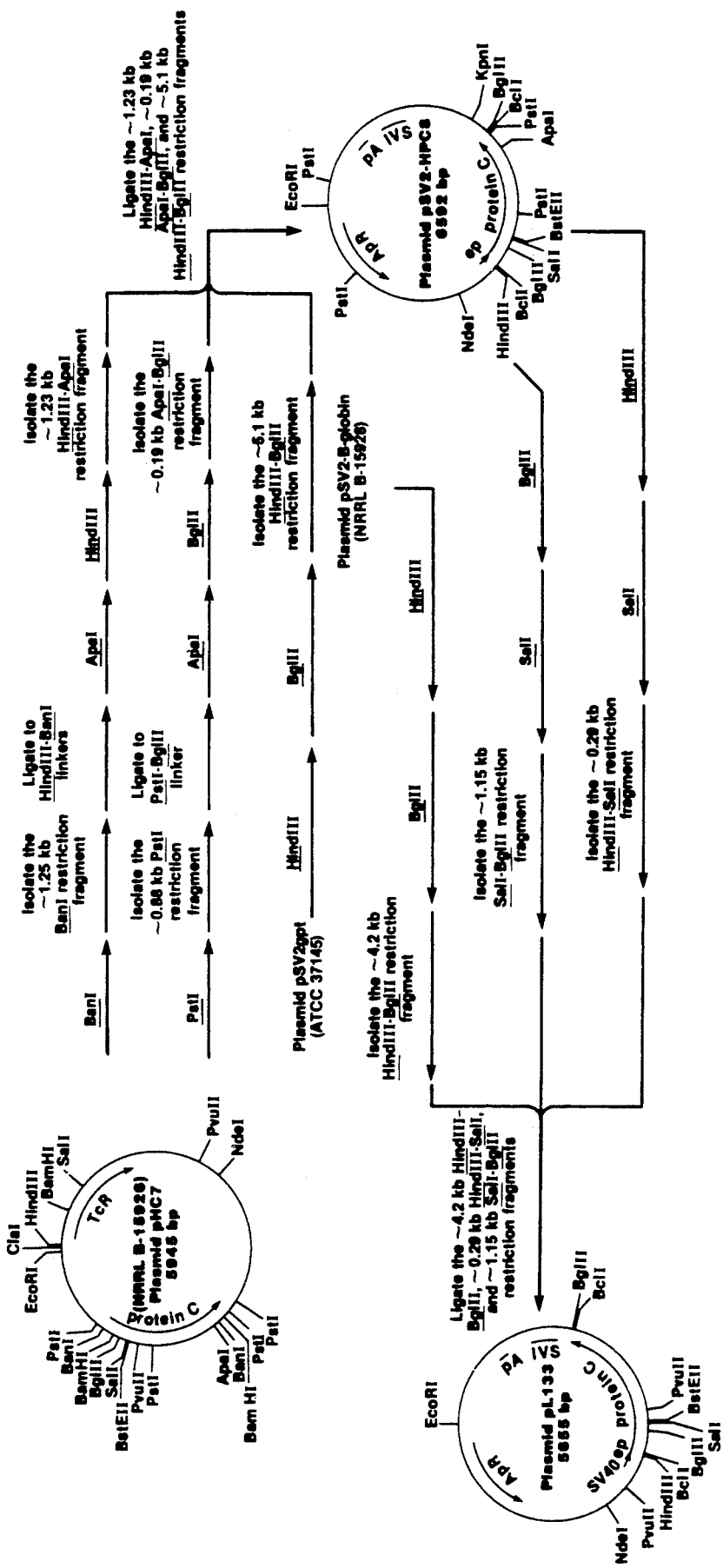
FIG. 2 schematically illustrates the construction of plasmid pL133, a starting material used in the construction of plasmid pLPC.

The ~1 mg of plasmid pHC7 DNA obtained by this procedure was suspended in 1 ml of TE buffer (10 mM Tris-HCl, pH=7.6, and 0.1 mM EDTA) and stored at −20° C. A restriction site and function map of plasmid pHC7 is presented in FIG. 2 of the accompanying drawings.

About 7 μg (7 μl) of plasmid pHC7 DNA were added to 25 μl of 10X Core buffer TM (Core buffer TM, BRL, is 500 mM Tris-HCl, pH=8.0; 500 mM NaCl; and 100 mM $MgCl_2$), 198 μl of $H_2O$, and 12 μl of restriction enzyme SstI (~60 units, Bethesda Research Laboratories (BRL), Gaithersburg, Md. 20877; all enzymes referred to in these Examples are available, unless otherwise indicated, from BRL or New England Biolabs (NEB), Beverly, Mass. 01915-9990, and are used in substantial accordance with the manufacturer's recommendations), and 8 μl (80 units) of restriction enzyme SalI. The reaction mixture was incubated at 37° C. for four hours; then, the SstI-SalI digested plasmid pHC7 DNA was extracted first with phenol and then with chloroform, collected by precipitation with ethanol and centrifugation, and finally suspended in 15 μl of TE/10 buffer (10 mM Tris-base, pH=7.6, and 0.1 mM EDTA) buffer.

The reaction mixture was then electrophoresed on an ~0.6% low-gelling-temperature agarose (FMC Corporation, Marine Colloids Division, Rockland, Me. 04841) gel for 2-3 hours at ~130 V and ~65 mA in Tris-Acetate buffer. The gel was stained in a dilute solution of ethidium bromide, and the band of DNA constituting the ~0.7 kb SstI-SalI restriction fragment, which was visualized with long-wave UV light, was cut from the gel in a small segment. The volume of the segment was determined by weight and density of the segment, and four volumes of TE containing 0.25M NaCl were added to the tube containing the segment. The segment was then melted by incubation at 72° C. About 0.5 μg of the ~0.7 kb SstI-SalI restriction fragment of plasmid pHC7 was obtained in a volume of about 400 μl. Further purification of the DNA was obtained by passing the solution of DNA through a NACS-prepac® column (BRL) in accordance with the manufacturer's recommendations; the purified fragment was resuspended in 15 μl of deionized water.

B. Construction of Recombinant Phage and Removal of the Activation Peptide-encoding DNA by Site-Specific Mutagenesis About 1 μg of phage M13mp18 (obtained from New England Biolabs) RF (replicative form) DNA was digested with restriction enzymes SstI and SalI in substantial accordance with the procedure described in Example 1A. The reaction was stopped by extracting the reaction mixture with phenol and then chloroform; then, the DNA was precipitated, collected by centrifugation, and resuspended in about 15 μl of TE buffer. The two fragments resulting from the digestion were separated on an ~0.6% low-gelling-temperature agarose gel, and the larger fragment was cut out from the gel and purified as described in Example 1A.

About 0.1 μg (in 7 μl of $H_2O$) of the ~0.7 kb SstI-SalI restriction fragment of plasmid pHC7 was added to 5 μl of the SstI-SalI-digested M13mp18 RF DNA together with 2 μl of 10X ligase buffer (0.5M Tris-HCl, pH=7.8; 60 mM $MgCl_2$; and 0.2M dithiothreitol (DTT)), 2 μl of 1 mg/ml BSA, 1 μl of 25 mM ATP, 1 μl (~400 units) of T4 DNA ligase (NEB), and 2 μl of $H_2O$. The ligation reaction was incubated at 25° C. overnight; the ligated DNA constituted the desired phage M13mp18-HE1 DNA in double-stranded form.

About 300 μl of an overnight culture of E. coli K12 JM101 (New England Biolabs) were used to inoculate 30 ml of 2X TY broth (TY broth is 10 g/L tryptone, 10 g/L NaCl, and 5 g/L yeast extract), and the resulting culture was incubated at 37° C. with aeration until the $O.D._{600}$ was ~0.5. The culture was chilled for 10 minutes in an ice-water bath, collected by centrifugation, and resuspended in 15 ml of cold, 10 mM NaCl. The cells were again collected by centrifugation and then resuspended in 15 ml of cold, 30 mM $CaCl_2$. The cells were placed on ice for 20 minutes and collected by centrifugation. The cells were resuspended in 1.5 ml of cold, 30 mM $CaCl_2$; a 200 μl aliquot of the cells was removed, added to 9 μl of the ligated DNA prepared above, and incubated on ice for about 30 minutes. The cell-DNA mixture was then incubated at 42° C. for 2 minutes and then added to 3 ml of top agar (TY broth with 0.5% agar kept molten at 45° C.) that also contained 50 μl of 2% X-Gal ("X-Gal" is 5-Bromo-4-chloro-3-indolyl-β-D-galactopyranoside), 50 μl of 100 mM IPTG ("IPTG" is isopropyl β-D-thiogalactopyranoside), and 100 μl of E. coli K12 JM101 in logarithmic growth phase. The cell-top agar mixture was then plated on TY-agar plates, and the plates were incubated at 37° C. overnight.

The following morning, four clear plaques were individually used to inoculate 2 ml of 2X TY broth, and the resulting cultures were incubated at 37° C. with aeration for 6 hours. Then, the cultures were centrifuged, and 500 μl of the resulting supernatant (the cell pellets were used to prepare phage DNA for restriction enzyme analysis) were added to 500 μl cultures ($O.D._{550}$=0.5) of E. coli K12 JM101 and 50 ml of 2X TY broth. These cultures were incubated overnight at 37° C. The phage RF DNA was isolated from the cell pellets using a scaled-down version of the procedure described in Example 1A, except that no antibiotic was used in the culture media, and the ultracentrifugation steps were replaced with phenol and chloroform extractions. Transformants containing phage M13mp18-HE1 DNA were identified by restriction enzyme analysis of their phage DNA.

The overnight cultures were centrifuged, and about 1 ml of a solution composed of 20% polyethylene glycol (PEG) 6000 and 2.5 mM NaCl was added per 5 ml of supernatant, which was then incubated at room temperature for 10 minutes. The mixture was centrifuged for 10 minutes at 10,000 r.p.m., and the resulting pellet, which contained single-stranded phage M13mp18-HE1 DNA, was resuspended in 500 μl of TES buffer (20 mM Tris-HCl, pH=7.5; 0.1M EDTA; and 10 mM NaCl). The DNA solution was extracted first with chloroform, then twice with TE-saturated phenol, and then again with chloroform. The single-stranded DNA was then precipitated using NaOAc and ethanol, centrifuged, and, after the pellet was washed with 70% ethanol and dried, the resulting pellet was dissolved in 80 μl of $H_2O$. This phage preparation was used in the next step, the site-specific mutagenesis, to remove the activation peptide-encoding DNA.

The single-stranded DNA fragment used in the mutagenesis to remove the activation peptide-encoding DNA was synthesized on an automated DNA synthesizer and is depicted below:

5'-GCGCAGTCACCTGAAACGACTCATT-
GATGGGAAGATGA-3'.

About 30 picomoles (1 μl) of the single-stranded DNA fragment depicted above (the "mutagenic oligonucleotide") and 1.5 μl (7.5 picomoles) of the M13 universal primer (marketed by Boehringer-Mannheim Biochemicals (BMB), 7941 Castleway Drive, P.O. Box 50816, Indianapolis, Ind. 46250) were individually treated with 5 units (Pharmacia, P-L Biochemicals, Inc., 800 Centennial Avenue, Piscataway, N.J. 08854) of T4 polynucleotide kinase in 10 μl of 1X kinase buffer (100 mM Tris-HCl, pH=8.3; 100 mM DDT; and 100 mM $MgCl_2$) containing 1 μl of 1 mM ATP for 30 minutes at 37° C., followed by a 10 minute, 65° C. incubation and subsequent freezing. The kinase-treated DNAs were used in the mutagenesis procedure described below.

In the first step of the mutagenesis procedure, the mutagenic oligonucleotide and the M13 universal primer were annealed to the single-stranded phage DNA. The annealing reaction was carried out by adding 300 nanograms (0.5 μl) of single-stranded phage M13mp18-HE1 to 1 picomole (1.2 μl) of the universal primer, 1 picomole (0.3 μl) of the mutagenic oligonucleotide, 2 μl of 10X annealing buffer (100 mM Tris-HCl, pH=7.5; 1 mM EDTA; and 500 mM NaCl), and 16 μl of $H_2O$, incubating the mixture at 80° C. for 2 minutes and then at 50° C. for 5 minutes, and, finally, allowing the mixture to cool to room temperature.

Once the oligonucleotides were annealed, the phage DNA was made double-stranded by extending the primers with DNA polymerase. The extension reaction was carried out by adding 3 μl of 10X extension buffer (500 mM Tris-HCl, pH=8; 1 mM EDTA; and 120 mM $MgCl_2$); 3 μl of 10X ligase buffer; 1.5 μl of 0.2 mM DTT; 3 μl of dNTP mix (0.5 mM in each dNTP); 1.2 μl of 25 mM ATP; 0.5 μl of Klenow enzyme (5 U/μl, BMB); 1 μl of T4 DNA ligase (400 U, NEB); and 19.8 μl of $H_2O$ to the mixture of annealed DNA. The extension reaction was incubated at room temperature for 30 minutes, then at 37° C. for 4 hours, and then overnight at 4° C.

The reaction was stopped by a phenol-chloroform extraction and precipitation of the DNA with ethanol and sodium acetate (NaOAc). The DNA was collected by centrifugation and resuspended in 40 μl of S1 buffer (0.3M NaCl; 0.03M NaOAc, pH=4.5; and 0.3 mM $ZnCl_2$) were then added to the solution of DNA. The S1 treatment described below has been reported to be beneficial in site-specific mutagenesis procedures. However, the present inventors found no significant advantage in the S1 treatment and, in the construction protocols described in subsequent Examples herein, omitted the S1 treatment entirely.

The solution of DNA was split equally into two tubes, and to one of the tubes, 100 units (BMB) of S1 nuclease were added. The S1 reaction was incubated at room temperature for 5 minutes and stopped by extracting the reaction mixture once with TE-saturated phenol-chloroform (50:50). The DNA was precipitated from the reaction mixture and from the non-S1-treated sample with NaOAc and ethanol.

The DNA pellets were resuspended in 60 μl of $H_2O$ and used to transform E. coli K12 JM101 in accordance with the procedure used during the construction of phage M13mp18-HE1, except that no IPTG or X-Gal was added to the plates. The mutants were screened for by using a small portion of the mutagenic oligonucleotide, 5'-TGAAACGACTCATTGA-3' (radioactively labelled), as a probe in plaque and dot-blot hybridizations. Several plaques that appeared positive from the hybridizations were picked and individually inoculated into 2 ml of a culture of E. coli K12 JM101 in logarithmic growth phase. These cultures were incubated at 37° C. with aeration for about 6 hours, when they were then used to prepare single-stranded DNA as described above for phage M13mp18-HE1.

The single-stranded DNA was sequenced using the dideoxy-sequencing method (J. H. Smith, 1980, Methods in Enzymology 65:560–580). Several phage were identified with the desired mutation. Phage in which the coding sequence for the activation peptide was deleted were designated phage M13mp18-HE2. The mutation in phage M13mp18-HE2 causes a decrease in size of 36 bp with respect to the natural coding sequence, a difference that can be used to facilitate identification of DNA that contains the mutated region. The RF form of phage M13mp18-HE2 was prepared for use in subsequent constructions.

C. Final Construction of Plasmid pLAPC From Phage M13mp18-HE2 and Plasmid pLPC

The mutagenized SstI-SalI (~0.7 kb) restriction fragment of the RF form of phage M13mp18-HE2 was cut from the phage and isolated in substantial accordance with the procedure of Example 1A. However, the ~100 μl of solution containing ~0.1 μg of the desired 0.7 kb fragment in a 1:2 dilution of low-gelling agarose were not passed through any purification column but were used directly in the ligation to produce plasmid pLAPC, described below.

Three DNA fragments were ligated together to form plasmid pLAPC: the ~0.7 kb SstI-SalI restriction fragment of phage M13mp18-HE2, described above, and two DNA fragments from plasmid pLPC. The construction protocol for plasmid pLPC is described in Example 2. A restriction site and function map of plasmid pLPC is presented in FIG. 1 of the accompanying drawings. Because of the positioning of SalI, SstI, and EcoRI restriction enzyme recognition sites on plasmid pLPC, the desired EcoRI-SalI and EcoRI-SstI restriction fragments had to be prepared in two separate digestions.

To prepare the EcoRI-SstI fragment, about 40 μg of plasmid pLPC in 25 μl of $H_2O$ were added to 10 μl of 1 mg/ml BSA, 10 μl of 10X Core buffer TM (BRL), 5 μl of restriction enzyme EcoRI (50 U, BRL), 5 μl of restriction enzyme SstI (25 U, BRL), and 45 μl of $H_2O$, and the resulting reaction was incubated at 37° C. for 1.5 hours. The SstI-EcoRI-digested plasmid pLPC DNA was collected by precipitation with ethanol and centrifugation. The SstI-EcoRI-digested DNA was resuspended in water and then loaded onto an ~0.6% low-gelling-temperature agarose gel to separate the DNA fragments by electrophoresis.

To prepare the EcoRI-SalI fragment, about 15 μg of plasmid pLPC in 9 μl of $H_2O$ were first treated with restriction enzyme ApaI to eliminate contamination by similarly-sized restriction fragments. About 10 μl of 10X ApaI buffer (60 mM NaCl; 60 mM Tris-HCl, pH=7.4; 60 mM MgCl₂; and 60 mM DTT), 10 μl of 1 mg/ml BSA, 69 μl of H₂O, and 2 μl of restriction enzyme ApaI (50 U, NEB) were added to the solution of plasmid pLPC DNA, and the resulting reaction was incubated at 37° C. for one hour. Then, 15 μl of 2M NaCl, 69 μl of H₂O, 8 μl of restriction enzyme SalI (NEB), and 8 μl of restriction enzyme EcoRI (NEB), were added to the solution of ApaI-digested plasmid pLPC DNA, and the resulting reaction was incubated at 37° C. for one hour. The ApaI-SalI-EcoRI-digested plasmid pLPC DNA was extracted first with phenol and then with chloroform, then collected by precipitation with ethanol and centrifugation, and finally resuspended in 25 μl of H₂O. The DNA was then loaded onto an ~0.6% low-gelling-temperature agarose gel and the DNA fragments separated by electrophoresis.

The ~3.76 kb EcoRI-SalI and the ~2.0 kb EcoRI-SstI restriction fragments were cut from the gels and the gel fragments melted after adding equal volumes of 10 mM Tris-HCl, pH=7.6, as described in Example 1A. About 2 μg of the ~3.76 kb EcoRI-SalI restriction fragment of plasmid pLPC were thus obtained in ~200 μl of 10 mM Tris-HCl, pH=7.6, which also contained the melted agarose. About 2 μg of the ~2.0 kb EcoRI-SalI restriction fragment of plasmid pLPC were obtained in a separate ~200 μl of 10 mM Tris-HCl, pH=7.6, containing agarose.

About 12.5 μl of each solution of the two purified restriction fragments (the ~3.76 kb EcoRI-SalI restriction fragment of plasmid pLPC and the ~2.0 kb EcoRI-SstI restriction fragment of plasmid pLPC) were added to 20 μl of the ~0.7 kb SstI-SalI restriction fragment of phage M13mp18-HE2, 10 μl of 1 mg/ml BSA, 10 μl of 10 mM ATP, 10 μl of 10X ligase buffer, 2 μl (~800 U, NEB) of T4 DNA ligase, and 23 μl of H₂O, and the resulting ligation reaction was incubated at 15° C. overnight. The ligated DNA constituted the desired plasmid pLAPC. Plasmid pLAPC only differs from plasmid pLPC (FIG. 1) in the deletion of the activation peptide-encoding DNA.

To check plasmid structure and obtain large amounts of plasmid pLAPC for eukaryotic cell transformation and further constructions, the ligated DNA containing plasmid pLAPC was used to transform *E. coli* K12 RV308, available from the NRRL under the accession number NRRL B-15624.

A 50 ml culture of *E. coli* K12 RV308 in L broth was grown to an optical density (O.D.) at 590 nm of ~0.6. The culture was chilled on ice for ten minutes, and the cells were collected by centrifugation. The cell pellet was resuspended in 25 ml of cold, 10 mM NaCl. The cells were again pelleted by centrifugation, and the pellet was resuspended in 25 ml of cold, 30 mM CaCl₂ and incubated on ice for 30 minutes. The cells were again collected by centrifugation and resuspended in 2.5 ml of cold, 30 mM CaCl₂.

Two hundred μl of this cell suspension were mixed with the ligated DNA containing plasmid pLAPC and incubated on ice for 60 minutes. The mixture was then incubated at 42° C. for 2 minutes, followed by a 10 minute incubation at room temperature. About 10 ml of 2X TY broth were added to the cell-DNA mixture, and then the cells were incubated in an air-shaker incubator in a 125 ml flask at 37° C. for two hours.

Aliquots of the cell mixture were plated on TY-agar (TY broth with 15 g/l agar) plates containing 100 μg/ml ampicillin, and the plates were then incubated at 37° C. overnight. *E. coli* K12 RV308/pLAPC transformants were verified by restriction enzyme analysis of their plasmid DNA. Plasmid DNA was obtained from the *E. coli* K12 RV308/pLAPC transformants in substantial accordance with the teaching of Example 1A, except that 50 μg/ml of ampicillin, and not tetracycline, was used as the selective agent.

EXAMPLE 2

The Construction of Plasmid pLPC

Plasmid pLPC was used as an intermediate vector in the construction of plasmid pLAPC (see Example 1C). Plasmid pLPC comprises a segment of DNA that encodes the BK virus enhancer and the adenovirus 2 late promoter positioned to drive expression of human protein C. The construction protocol for plasmid pLAPC essentially results in the replacement of the human protein C coding sequence on plasmid pLPC with another protein C coding sequence from which the activation peptide-encoding DNA has been removed.

The BK enhancer/adenovirus late promoter expression control sequences on plasmids pLPC and pLAPC are the subject matter of U.S. patent application Ser. No. 06/849,999, filed Apr. 9, 1986, attorney docket number X-6606. U.S. patent application Ser. No. 06/849,999 discloses that the expression control sequence of plasmid pLPC (and thus pLAPC) is greatly stimulated in its activity by the presence of an immediate early gene product of a large DNA virus, i.e., the E1A gene product of adenovirus.

The construction protocol for plasmid pLPC is set forth below. The entire construction protocol for plasmid pLPC is schematically illustrated in FIG. 1 of the accompanying drawings. In brief, Example 2A describes the isolation of BK virus DNA, from which the BK enhancer can be obtained. Example 2B sets forth the construction protocol for plasmid pBKneo1, a plasmid resulting from the insertion of the BK enhancer into plasmid pdBPV-MMTneo. Example 2C teaches the construction protocol for plasmid pLPcat, a plasmid resulting from the insertion of the adenovirus 2 late promoter into plasmid pSV2cat. Example 2D teaches the construction protocol for plasmid pBLcat, a plasmid that contains the BK enhancer positioned to stimulate the activity of the adenovirus late promoter. Example 2E describes the construction protocol for plasmid pL133, a protein C expression vector, beginning with starting material plasmid pHC7 and proceeding through the construction of intermediate plasmid pSV2-HPC8 and then the final construction of plasmid pL133. Finally, Example 2F teaches the construction protocol for plasmid pLPC, which comprises the BK enhancer/adenovirus late promoter expression control sequence of plasmid pBLcat inserted into plasmid pL133 to drive expression of human protein C.

A. Preparation of BK Virus DNA

BK virus is obtained from the American Type Culture Collection under the accession number ATCC VR-837. The virus is delivered in freeze-dried form and resuspended in Hank's balanced salts (Gibco, 3175 Staley Road, Grand Island, N.Y. 14072) to a titer of about 10⁵ plaque-forming units (pfu)/ml. The host of choice for the preparation of BK virus DNA is primary human embryonic kidney (PHEK) cells, which can be obtained from Flow Laboratories, Inc., 7655 Old Springhouse Road, McLean, Va. 22101, under catalogue number 0-100 or from M.A. Bioproducts under catalogue number 70-151.

About five 75 mm² polystyrene flasks comprising confluent monolayers of about 10⁶ PHEK cells are used to prepare the virus. About 1 ml of BK virus at a titer of 10⁵ pfu/ml is added to each flask, which is then incubated at 37° C. for one hour, and then, fresh culture medium (Dulbecco's Modified Eagle Medium, Gibco, Grand Island, N.Y. 14072, supplemented with 10% fetal bovine serum) is added, and the infected cells are incubated at 37° C. for 10-14 days or until the full cytopathogenic effect of the virus is noted. This cytopathogenic effect varies from cell line to cell line and from virus to virus but usually consists of cells rounding up, clumping, and sloughing off the culture disk.

The virus is released from the cells by three freeze-thaw cycles, and the cellular debris is removed by centrifugation at 5000Xg. The virus in 1 liter of supernatant fluid is precipitated and collected by the addition of 100 g of PEG-6000, incubation of the solution for 24 hours at 4° C., and centrifugation at 5000Xg for 20 minutes. The pellet is dissolved in 0.1X SSC buffer (1XSSC=0.15M NaCl and 0.015M NaCitrate, pH=7) at 1/100th of the original volume. The virus suspension is layered onto a 15 ml solution of saturated KBr in a tube, which is centrifuged at 75,000Xg for 3 hours. Two bands are evident in the KBr solution after centrifugation. The lower band, which contains the complete virion, is collected and desalted on a Sephadex ® G-50 column (Sigma Chemical Co., St. Louis, Mo. 63178) using TE (10 mM Tris-HCl, pH=7.8, and 1 mM EDTA) as an elution buffer.

Sodium dodecyl sulfate (SDS) is added to the solution of purified virions obtained from the column to a concentration of 1%; pronase ® (Sigma) protease is added to a concentration of 100 μg/ml, and the solution is incubated at 37° C. for 2 hours. Cesium chloride is then added to the solution to a density of 1.56 g/ml, and ethidium bromide is added to the solution to a final concentration of 100 μg/ml. The solution is centrifuged in a Sorvall 865 rotor (DuPont Co., Newton, Conn. 06470) or similar vertical rotor at 260,000Xg for 24 hours. After centrifugation, the band of virus DNA is isolated and extracted five times with isoamyl alcohol saturated with 100 mM Tris-HCl, pH=7.8. The solution of BK virus DNA is then dialyzed against TE buffer until the 260 nm/280 nm absorbance ratio of the DNA is between 1.75 and 1.90. The DNA is precipitated by adjusting the NaCl concentration to 0.15M, adding two volumes of ethanol, incubating the solution at −70° C. for at least 2 hours, and centrifuging the solution at 12,000Xg for 10 minutes. The resulting pellet of BK virus DNA is suspended in TE buffer at a concentration of 1 mg/ml. A restriction site and function map of BK virus is presented in FIG. 1 of the accompanying drawings.

B. Construction of Plasmid pBKneo1

*E. coli* K12 HB101/pdBPV-MMTneo cells are obtained in lyophilized form from the American Type Culture Collection under the accession number ATCC 37224. The lyophilized cells are plated on L-agar plates containing 100 μg/ml ampicillin and incubated at 37° C. to obtain single colony isolates.

One liter of L broth (10 g tryptone, 10 g NaCl, and 5 g yeast extract per liter) containing 50 μg/ml ampicillin was inoculated with a colony of *E. coli* K12 HB101/pdBPV-MMTneo and incubated in an air-shaker at 37° C. until the $O.D._{590}$ was ~1 absorbance unit, at which time 150 mg of chloramphenicol were added to the culture. The incubation was continued for about 16 hours; the chloramphenicol addition inhibits protein synthesis, and thus inhibits further cell division, but allows plasmid replication to continue. Plasmid pdBPV-MMTneo DNA was then prepared from the culture in substantial accordance with the procedure described in Example 1A.

The ~1 mg of plasmid pdBPV-MMTneo DNA obtained by this procedure was suspended in 1 ml of TE buffer and stored at −20° C. The plasmid isolation procedure described in Example 1A is generally used when large amounts of very pure plasmid DNA are desired. The procedure can be modified to obtain rapidly a smaller, less pure amount of DNA, such as is needed when screening transformants for the presence of a given plasmid, by using only about 5 ml of cultured cells, lysing the cells in an appropriately scaled-down amount of lysis buffer, and replacing the centrifugation steps with phenol and chloroform extractions.

About 5 μg (5 μl) of the plasmid pdBPV-MMTneo DNA prepared as described above and five μg (5 μl) of the BK virus DNA prepared as described above were each digested at 37° C. for 2 hours in a solution containing 2 μl of 10X BamHI buffer (1.5M NaCl; 60 mM Tris-HCl, pH=7.9; 60 mM MgCl₂; and 1 mg/ml BSA), 1 μl (~10 units) of restriction enzyme BamHI, and 7 μl of H₂O. The reaction was stopped by an extraction with an equal volume of phenol, followed by two extractions with chloroform. Each BamHI-digested DNA was then precipitated, collected by centrifugation, and resuspended in 5 μl of H₂O.

About 1 μl of 10X ligase buffer was added to a mixture of BamHI-digested plasmid pdBPV-MMTneo (1 μl) and BamHI-digested BK virus DNA (1 μl). After 1 μl (~5 units) of T4 DNA ligase and 6 μl of H₂O were added to the mixture of DNA, the resulting reaction was incubated at 16° C. overnight. The ligated DNA constituted the desired plasmids pBKneo1 and pBKneo2, which differ only with respect to the orientation of the BK virus DNA. A restriction site and function map of plasmid pBKneo1 is presented in FIG. 1 of the accompanying drawings.

*E. coli* K12 HB101 cells are available in lyophilized form from the Northern Regional Research Laboratory under the accession number NRRL B-15626. A 50 ml culture of *E. coli* K12 HB101 in L broth was grown to an optical density at 650 nanometers ($O.D._{650}$) of approximately 0.4 absorbance units. The culture was chilled on ice for ten minutes, and the cells were collected by centrifugation. The cell pellet was resuspended in 25 ml of cold 100 mM MgCl₂ and incubated on ice for 25 minutes. The cells were once again pelleted by centrifugation, and the pellet was resuspended in 2.5 ml of cold 100 mM CaCl₂ and incubated for 30 minutes on ice. After the incubation, the cells are competent for the uptake of transforming DNA.

Two hundred μl of this cell suspension were mixed with the ligated DNA prepared above and incubated on ice for 30 minutes. At the end of this period, the cells were placed in a water bath at 42° C. for 2 minutes and then returned to the ice for an additional 10 minutes. The cells were collected by centrifugation and resuspended in one ml of L broth and incubated at 37° C. for 1 hour. The transformed cells were plated on L-agar plates containing 100 μg/ml ampicillin. *E. coli* K12

HB101/pBKneo1 and E. coli K12/pBKneo2 transformants were identified by their ampicillin-resistant phenotype and by restriction enzyme analysis of their plasmid DNA. A restriction site and function map of plasmid pBKneo1 is presented in FIG. 1, Part A, of the accompanying drawings.

C. Construction of Plasmid pLPcat, an Intermediate Plasmid Used in the Construction of Plasmid pBLcat The virion DNA of adenovirus 2 (Ad2) is a double-stranded linear molecule about 35.94 kb in size. The Ad2 late promoter can be isolated on an ~0.32 kb AccI-PvuII restriction fragment of the Ad2 genome; this ~0.32 kb restriction fragment corresponds to the sequence between nucleotide positions 5755 and 6071 of the Ad2 genome. To isolate the desired ~0.32 kb AccI-PvuII restriction fragment, Ad2 DNA is first digested with restriction enzyme BalI, and the ~2.4 kb BalI restriction fragment that comprises the entire sequence of the ~0.32 kb AccI-PvuII restriction fragment is isolated. Then, the ~2.4 kb BalI restriction fragment is digested with AccI and PvuII to obtain the desired fragment.

About 50 μg of Ad2 DNA (available from BRL) are dissolved in 80 μl of $H_2O$ and 10 μl of 10X BalI buffer (100 mM Tris-HCl, pH=7.6; 120 mM $MgCl_2$; 100 mM DTT; and 1 mg/ml BSA). About 10 μl (~20 units) of restriction enzyme BalI are added to the solution of Ad2 DNA, and the resulting reaction is incubated at 37° C. for 4 hours.

The BalI-digested DNA is loaded onto an agarose gel and electrophoresed until the restriction fragments are well separated. Visualization of the electrophoresed DNA is accomplished by staining the gel in a dilute solution (0.5 μg/ml) of ethidium bromide and exposing the stained gel to long wave ultraviolet (UV) light. One method to isolate DNA from agarose is as follows. A small slit is made in the gel in front of the desired fragment, and a small piece of NA-45 DEAE membrane (Schleicher and Schuell, Keene, N.H. 03431) is placed in each slit. Upon further electrophoresis, the DNA non-covalently binds to the DEAE membrane. After the desired fragment is bound to the DEAE membrane, the membrane is removed and rinsed with low-salt buffer (100 mM KCl; 0.1 mM EDTA; and 20 mM Tris-HCl, pH=8). Next, the membrane is placed in a small tube and immersed in high-salt buffer (1M NaCl; 0.1 mM EDTA; and 20 mM Tris-HCl, pH=8) and then incubated at 65° C. for one hour to remove the DNA from the DEAE paper. After the 65° C. incubation, the incubation buffer is collected and the membrane rinsed with high-salt buffer. The high-salt rinse solution is pooled with the high-salt incubation buffer.

The volume of the high salt-DNA solution is adjusted so that the NaCl concentration is 0.25M, and then three volumes of cold, absolute ethanol are added to the solution. The resulting solution is mixed and placed at −70° C. for 10–20 minutes. The solution is then centrifuged at 15,000 rpm for 15 minutes. After another precipitation to remove residual salt, the DNA pellet is rinsed with ethanol, dried, resuspended in 20 μl of TE buffer, and constitutes about 3 μg of the desired restriction fragment of Ad2. The purified fragment obtained is dissolved in 10 μl of TE buffer.

About 6 μl of $H_2O$ and 2 μl of 10X AccI buffer (60 mM NaCl; 60 mM Tris-HCl, pH=7.5; 60 mM $MgCl_2$; 60 mM DTT; and 1 mg/ml BSA) are added to the solution of the ~2.4 kb BalI restriction fragment of Ad2. After the addition of about 2 μl (~10 units) of restriction enzyme AccI to the solution of DNA, the reaction is incubated at 37° C. for 2 hours. After the AccI digestion, the DNA is collected by ethanol precipitation and resuspended in 16 μl of $H_2O$ and 2 μl of 10X PvuII buffer (600 mM NaCl; 60 mM Tris-HCl, pH=7.5; 60 mM $MgCl_2$; 60 mM DTT; and 1 mg/ml BSA). After the addition of about 2 μl (about 10 units) of restriction enzyme PvuII to the solution of DNA, the reaction is incubated at 37° C. for 2 hours.

The AccI-PvuII-digested, ~2.4 kb BalI restriction fragment of Ad2 is loaded onto an ~6% polyacrylamide gel and electrophoresed until the ~0.32 kb AccI-PvuII restriction fragment that comprises the Ad2 late promoter is separated from the other digestion products. The gel is stained with ethidium bromide and viewed using UV light, and the segment of gel containing the ~0.32 kb AccI-PvuII restriction fragment is cut from the gel, crushed, and soaked overnight at room temperature in ~250 μl of extraction buffer (500 mM $NH_4OAc$; 10 mM MgOAc; 1 mM EDTA; and 0.1% SDS). The following morning, the mixture is centrifuged, and the pellet is discarded. The DNA in the supernatant is precipitated with ethanol; about 2 μg of tRNA are added to ensure complete precipitation of the desired fragment. About 0.2 μg of the ~0.32 kb AccI-PvuII restriction fragment are obtained and suspended in 7 μl of $H_2O$.

To convert the AccI-PvuII restriction fragment to an AccI-BclI restriction fragment, BclI linkers were ligated to the ~0.32 AccI-PvuII restriction fragment. Because the BclI linkers were blunt-ended, the linkers only attached to the PvuII end of the restriction fragment. The BclI linkers (New England Biolabs), which had the following sequence:

were kinased and prepared for ligation by the following procedure. Four μl of linkers (~2 μg) were dissolved in 20.15 μl of $H_2O$ and 5 μl of 10X kinase buffer (500 mM Tris-HCl, pH=7.6 and 100 mM $MgCl_2$), incubated at 90° C. for two minutes, and then cooled to room temperature. Five μl of $\gamma$-$^{32}$P-ATP (~20 μCi), 2.5 μl of 1M DTT, and 5 μl of polynucleotide kinase (~10 units) were added to the mixture, which was then incubated at 37° C. for 30 minutes. Then, 3.35 μl of 0.01M ATP and 5 μl of kinase were added, and the reaction was continued for another 30 minutes at 37° C. The radioactive ATP aids in determining whether the linkers have ligated to the target DNA.

About 0.25 μg (in 0.5 μl) of the kinased BclI linkers was added to the solution of the ~0.32 kb AccI-PvuII restriction fragment, and then, 1 μl (~1000 units) of T4 DNA ligase and 1 μl of 10X ligase buffer were added to the solution of DNA, and the resulting reaction was incubated at 16° C. overnight. The BclI linkers could only ligate to the PvuII end of the AccI-PvuII restriction fragment. DNA sequencing later revealed that four BclI linkers attached to the PvuII end of the AccI-PvuII restriction fragment. These extra BclI linkers can be removed by BclI digestion and religation; however, the extra BclI linkers were not removed as the linkers do not interfere with the proper functioning of the vectors that comprise the extra linkers.

E. coli K12 HB101/pSV2cat cells are obtained in lyophilized form from the ATCC under the accession number ATCC 37155, and plasmid pSV2cat DNA was isolated from the cells in substantial accordance with the procedure of Example 1A, except that ampicillin, at 50 µg/ml, was used in place of tetracycline. A restriction site and function map of plasmid pSV2cat is presented in FIG. 1, Part B, of the accompanying drawings. About 1 mg of plasmid pSV2cat DNA is obtained and dissolved in 1 ml of TE buffer. About 3 µg (3 µl) of the plasmid pSV2cat DNA were added to 2 µl of 10X AccI buffer and 16 µl of $H_2O$, and then, 3 µl (about 9 units) of restriction enzyme AccI were added to the solution of pSV2cat DNA, and the resulting reaction was incubated at 37° C. for 2 hours. The AccI-digested plasmid pSV2cat DNA was then digested with restriction enzyme StuI by adding 3 µl of 10X StuI buffer (1.0M NaCl; 100 mM Tris-HCl, pH=8.0; 100 mM $MgCl_2$; 60 mM DTT; and 1 mg/ml BSA), 5 µl of $H_2O$, and about 2 µl (about 10 units) of restriction enzyme StuI. The resulting reaction was incubated at 37° C. for 2 hours. The reaction was terminated by extracting the reaction mixture once with phenol, then twice with chloroform. About 0.5 µg of the desired fragment was obtained and dissolved in 20 µl of TE buffer.

About 4 µl of the AccI-StuI-digested plasmid pSV2cat DNA were mixed with about 7 µl of the ~0.32 kb AccI-PvuII (with BclI linkers attached) restriction fragment of Ad2, and after the addition of 3 µl of 10X ligase buffer, 15 µl of $H_2O$, and 2 µl (about 1000 units) of T4 DNA ligase, the ligation reaction was incubated at 16° C. overnight. The ligated DNA constituted the desired plasmid pLPcat, a plasmid that comprises the Ad2 late promoter positioned so as to drive transcription, and thus expression, of the chloramphenicol acetyltransferase gene. A restriction site and function map of plasmid pLPcat is presented in FIG. 1, Part B, of the accompanying drawings.

The ligated DNA was used to transform E. coli K12 HB101 cells in substantial accordance with the procedure of Example 2B. The transformed cells were plated on L-agar plates containing 50 µg/ml ampicillin; restriction enzyme analysis of plasmid DNA was used to identify the E. coli K12 HB101/pLPcat transformants. Plasmid pLPcat DNA was isolated from the transformants for use in subsequent constructions in substantial accordance with the plasmid isolation procedure described in Example 1A, except that ampicillin was used as the selective agent in place of tetracycline.

D. Construction of Plasmid pBLcat

About 88 µg of plasmid pBKneol DNA in 50 µl of TE buffer were added to 7.5 µl of 10X AccI buffer, 30 µl of $H_2O$, and 15 µl (about 75 units) of restriction enzyme AccI, and the resulting reaction was incubated at 37° C. for 2 hours. The AccI-digested plasmid pBKneol DNA was loaded on an agarose gel, and the ~1.4 kb fragment that contains the BK enhancer was separated from the other digestion products. The ~1.4 kb AccI restriction fragment was then isolated from the gel and purified. About 5 µg of the fragment were resuspended in 5 µl of 10X PvuII buffer, 45 µl of $H_2O$, and 5 µl (about 25 units) of restriction enzyme PvuII, and the resulting reaction was incubated at 37° C. for 2 hours. The PvuII-digested DNA was then isolated, purified, and prepared for ligation. About 2 µg of the desired ~1.28 kb AccI-PvuII fragment were obtained and dissolved in 5 µl of TE buffer.

About 1 µg of plasmid pLPcat DNA was dissolved in 5 µl of 10X AccI buffer and 40 µl of $H_2O$. About 5 µl (~25 units) of restriction enzyme AccI were added to the solution of plasmid pLPcat DNA, and the resulting reaction was incubated at 37° C. The AccI-digested plasmid pLPcat DNA was precipitated with ethanol and resuspended in 5 µl of 10X StuI buffer, 40 µl of $H_2O$, and 5 µl (about 25 units) of restriction enzyme StuI, and the resulting reaction was incubated at 37° C. for 2 hours. The AccI-StuI-digested plasmid pLPcat DNA was precipitated with ethanol several times to purify the ~4.81 kb AccI-StuI restriction fragment that comprises the E. coli origin of replication and Ad2 late promoter away from the other digestion product, a restriction fragment about 16 bp in size. About 1 µg of the desired ~4.81 kb restriction fragment was obtained and dissolved in 20 µl of TE buffer.

The 5 µl of ~4.81 kb AccI-StuI restriction fragment of plasmid pLPcat were added to 5 µl of ~1.28 kb AccI-PvuII restriction fragment of plasmid pBKneol. After the addition of 3 µl of 10X ligase buffer, 15 µl of $H_2O$, and 2 µl (about 10 units) of T4 DNA ligase to the mixture of DNA, the resulting ligation reaction was incubated at 16° C. overnight. The ligated DNA constituted the desired plasmid pBLcat. A restriction site and function map of plasmid pBLcat is presented in FIG. 1, Part C, of the accompanying drawings.

The ligated DNA was used to transform E. coli K12 HB101 cells in substantial accordance with the procedure described in Example 2B. E. coli K12 HB101/pBLcat transformants were identified by restriction enzyme analysis of their plasmid DNA. Plasmid pBLcat DNA was prepared for use in subsequent constructions in substantial accordance with the procedure of Example 1A, except that ampicillin was used as the selective agent in place of tetracycline.

E. Construction of Plasmid pL133

Plasmid pL133 is a human protein C expression vector disclosed and claimed in U.S. patent application Ser. No. 06/699,967, filed Feb. 8, 1985, attorney docket No. X-6737. As described below, plasmid pL133 can be constructed using starting vector plasmids pSV2gpt and pHC7 (the preparation of plasmid pHC7 is described above in Example 1A) to construct intermediate vector plasmid pSV2-HPC8, which is then combined with plasmid pSV2-β-globin to yield plasmid pL133. The construction protocol for plasmid pL133 is described in detail, below, and schematically illustrated in FIG. 2 of the accompanying drawings.

Fifty µl (~50 µg) of plasmid pHC7 DNA were mixed with 5 µl (~50 units) of restriction enzyme BanI, 10 µl of 10X BanI reaction buffer (1.5M NaCl; 60 mM Tris-HCl, pH=7.9; 60 mM $MgCl_2$; and 1 mg/ml BSA), and 35 µl of $H_2O$ and incubated until the digestion was complete. The BanI-digested plasmid pHC7 DNA was then electrophoresed on a 3.5% polyacrylamide gel (29:1, acrylamide:bis-acrylamide), until the ~1.25 kb BanI restriction fragment was separated from the other digestion products.

The region of the gel containing the ~1.25 kb BanI restriction fragment was cut from the gel, placed in a test tube, and broken into small fragments. One ml of extraction buffer (500 mM $NH_4OAc$, 10 mM MgOAc, 1 mM EDTA, 1% SDS, and 10 mg/ml tRNA) was added to the tube containing the fragments, and the tube was placed at 37° C. overnight. Centrifugation was used to pellet the debris, and the supernatant was transferred to a new tube. The debris was washed once with 200 μl of extraction buffer; the wash supernatant was combined with the first supernatant from the overnight extraction. After passing the supernatant through a plug of glass wool, two volumes of ethanol were added to and mixed with the supernatant. The resulting solution was placed in a dry ice-ethanol bath for ~10 minutes, and then, the DNA was pelleted by centrifugation.

Approximately 8 μg of the ~1.25 kb BanI restriction fragment were obtained by this procedure. The purified fragment was suspended in 10 μl of TE buffer and stored at −20° C. The BanI restriction fragment had to be modified by the addition of a linker to construct plasmid pSV2-HPC8. The DNA fragments used in the construction of the linker were synthesized either by using a Systec 1450A DNA Synthesizer (Systec Inc., 3816 Chandler Drive, Minneapolis, Minn.) or an ABS 380A DNA Synthesizer (Applied Biosystems, Inc., 850 Lincoln Centre Drive, Foster City, Calif. 94404). Many DNA synthesizing instruments are known in the art and can be used to make the fragments. In addition, the fragments can also be conventionally prepared in substantial accordance with the procedures of Itakura et al., 1977, Science, 198:1056 and Crea et al., 1978, Proc. Nat. Acad. Sci. USA, 75:5765.

Five hundred picomoles of each single strand of the linker were kinased in 20 μl of reaction buffer, which contained 15 units (~0.5 μl) T4 polynucleotide kinase, 2 μl 1 10X ligase buffer, 10 μl of 500 μM ATP, and 7.5 μl of H₂O. The kinase reaction was incubated at 37° C. for 30 minutes, and the reaction was terminated by incubation at 100° C. for 10 minutes. To ensure complete kination, the reaction was chilled on ice, 2 μl of 0.2M dithiothreitol, 2.5 μl of 5 mM ATP, and 15 units of T4 polynucleotide kinase were added to the reaction mixture and mixed, and the reaction mixture was incubated another 30 minutes at 37° C. The reaction was stopped by another 10 minute incubation at 100° C. and then chilled on ice.

Although kinased separately, the two single strands of the DNA linker were mixed together after the kinase reaction. To anneal the strands, the kinase reaction mixture was incubated at 100° C. for 10 minutes in a water bath containing ~150 ml of water. After this incubation, the water bath was shut off and allowed to cool to room temperature, a process taking about 3 hours. The water bath, still containing the tube of kinased DNA, was then incubated at 4° C. overnight. This process annealed the single strands. The linker constructed had the following structure:

```
5'-AGCTTTGATCAG-3'
   ||||||||
3'-AACTAGTCCACG-5'
```

The linker was stored at −20° C. until use.

The ~8 μg of ~1.25 kb BanI fragment were added to and mixed with the ~50 μl of linker (~500 picomoles), 1 μl of T4 DNA ligase (~5 units), 10 μl of 10X ligase buffer, and 29 μl of H₂O, and the resulting ligation reaction was incubated at 4° C. overnight. The ligation reaction was stopped by a 10 minute incubation at 65° C. The DNA was pelleted by adding NaOAc to a final concentration of 0.3M, adding 2 volumes of ethanol, chilling in a dry ice-ethanol bath, and then centrifuging the solution.

The DNA pellet was dissolved in 10 μl of 10X ApaI reaction buffer (60 mM NaCl; 60 mM Tris-HCl, pH=7.4; 60 mM MgCl₂; and 60 mM 2-mercaptoethanol), 5 μl (~50 units) of restriction enzyme ApaI, and 85 μl of H₂O, and the reaction was placed at 37° C. for two hours. The reaction was then stopped and the DNA pelleted as above. The DNA pellet was dissolved in 10 μl of 10X HindIII reaction buffer, 5 μl (~50 units) of restriction enzyme HindIII, and 85 μl of H₂O, and the reaction was placed at 37° C. for two hours. After the HindIII digestion, the reaction mixture was loaded onto a 3.5% polyacrylamide gel, and the desired ~1.23 kb HindIII-ApaI restriction fragment was isolated from the gel and purified. Approximately 5 μg of the desired fragment were obtained, suspended in 10 μl of TE buffer, and stored at −20° C.

Fifty μl (~50 μg) of plasmid pHC7 DNA were mixed with 5 μl (~50 units) of restriction enzyme PstI, 10 μl of 10X PstI reaction buffer (1.0M NaCl; 100 mM Tris-HCl, pH=7.5; 100 mM MgCl₂; and 1 mg/ml BSA), and 35 μl of H₂O and incubated at 37° C. for two hours. The PstI-digested plasmid pHC7 DNA was then electrophoresed on a 3.5% polyacrylamide gel, and the desired ~0.88 kb fragment was purified in substantial accordance with the procedure described above. Approximately 5 μg of the desired fragment were obtained, suspended in 10 μl of TE buffer, and stored at −20° C.

The ~5 μg of ~0.88 kb PstI fragment were added to and mixed with ~50 μl of the following linker, which was constructed on an automated DNA synthesizer:

About 1 μl of T4 DNA ligase (~10 units), 10 μl 10X ligase buffer, and 29 μl H₂O were added to the mixture of DNA, and the resulting ligation reaction was incubated at 4° C. overnight.

The ligation reaction was stopped by a 10 minute incubation at 65° C. After precipitation of the ligated DNA, the DNA pellet was dissolved in 10 μl of 10X ApaI reaction buffer, 5 μl (~50 units) of restriction enzyme ApaI, and 85 μl of H₂O, and the reaction was placed at 37° for two hours. The reaction was then stopped and the DNA pelleted once again. The DNA pellet was dissolved in 10 μl 10X BglII reaction buffer (1M NaCl; 100 mM Tris-HCl, pH=7.4; 100 mM MgCl₂; 100 mM 2-mercaptoethanol; and 1 mg/ml BSA), 5 μl (~50 units) of restriction enzyme BglII, and 85 μl H₂O, and the reaction was placed at 37° C. for two hours. After the BglII digestion, the reaction mixture was loaded onto a 3.5% polyacrylamide gel, and the desired ~0.19 kb ApaI-BglII restriction fragment was isolated in substantial accordance with the procedure described above. Approximately 1 μg of the desired fragment was obtained, suspended in 10 μl of TE buffer, and stored at −20° C.

Approximately 10 μg of plasmid pSV2gpt DNA (ATCC 37145) were dissolved in 10 μl of 10X HindIII reaction buffer, 5 μl (~50 units) of restriction enzyme HindIII, and 85 μl of H₂O, and the reaction was placed at 37° C. for 2 hours. The reaction mixture was then made 0.25M in NaOAc, and after the addition of two volumes of ethanol and incubation in a dry ice-ethanol bath, the DNA was pelleted by centrifugation. The DNA pellet was dissolved in 10 μl of 10X BglII buffer, 5 μl (~50 units) of restriction enzyme BglII, and 85 μl of H₂O, and the reaction was placed at 37° C. for two hours. After the BglII digestion, the reaction mixture was loaded onto a 1% agarose gel, and the fragments were separated by electrophoresis. The gel was stained with ethidium bromide and viewed under ultraviolet light, and the band containing the desired ~5.1 kb HindIII-BglII fragment was cut from the gel and placed in dialysis tubing, and electrophoresis was continued until the DNA was out of the agarose. The buffer containing the DNA from the dialysis tubing was extracted with phenol and CHCl₃, and then, the DNA was precipitated. The pellet was resuspended in 10 μl of TE buffer and constituted ~5 μg of the desired ~5.1 kb HindIII-BglII restriction fragment of plasmid pSV2gpt.

Two μl of the ~1.23 kb HindIII-ApaI restriction fragment, 3 μl of the ~0.19 kb ApaI-BglII fragment, and 2 μl of the ~5.1 kb HindIII-BglII fragment were mixed together and then incubated with 10 μl of 10X ligase buffer, 1 μl of T4 DNA ligase (~500 units), and 82 μl of H₂O at 16° C. overnight. The ligated DNA constituted the desired plasmid pSV2-HPC8; a restriction site and function map of the plasmid is presented in FIG. 2 of the accompanying drawings.

*E. coli* K12 RR1 (NRRL B-15210) cells were made competent for transformation in substantial accordance with the procedure described for *E. coli* K12 HB101 in Example 2B. The ligated DNA prepared above was used to transform the cells, and aliquots of the transformation mix were plated on L-agar plates containing 100 μg/ml ampicillin. The plates were then incubated at 37° C. *E. coli* K12 RR1/pSV2-HPC8 transformants were verified by restriction enzyme analysis of their plasmid DNA. Plasmid pSV2-HPC8 DNA was prepared from the transformants in substantial accordance with the procedure of Example 1A, except that ampicillin, and not tetracycline, was used as the selective agent during culture of the cells.

Fifty μg of plasmid pSV2-HPC8 were dissolved in 10 μl of 10X HindIII reaction buffer, 5 μl (~50 units) of restriction enzyme HindIII, and 85 μl of H₂O, and the reaction was incubated at 37° C. for two hours. After the HindIII digestion, the DNA was precipitated, and the DNA pellet was dissolved in 10 μl of 10X SalI reaction buffer (1.5M NaCl; 60 mM Tris-HCl, pH=7.9; 60 mM MgCl₂; 60 mM 2-mercaptoethanol; and 1 mg/ml BSA), 5 μl (~50 units) of restriction enzyme SalI, and 85 μl of H₂O. The resulting SalI reaction mixture was incubated for 2 hours at 37° C. The HindIII-SalI-digested plasmid pSV2-HPC8 was loaded onto a 3.5% polyacrylamide gel and electrophoresed until the desired ~0.29 kb HindIII-SalI restriction fragment was separated from the other reaction products. The desired fragment was isolated from the gel; about 2 μg of the fragment were obtained and suspended in 10 μl of TE buffer.

Fifty μg of plasmid pSV2-HPC8 were dissolved in 10 μl of 10X BglII reaction buffer, 5 μl (50 units) of restriction enzyme BglII, and 85 μl of H₂O, and the reaction was incubated at 37° C. for two hours. After the BglII digestion, the DNA was precipitated, and the DNA pellet was dissolved in 10 μl of 10X SalI reaction buffer, 5 μl (~50 units) of restriction enzyme SalI, and 85 μl of H₂O. The resulting SalI reaction mixture was incubated for 2 hours at 37° C. The SalI-BglII-digested plasmid pSV2-HPC8 was loaded onto a 3.5% polyacrylamide gel and electrophoresed until the desired ~1.15 kb SalI-BglII restriction fragment was separated from the other reaction products. The ~1.15 kb SalI-BglII restriction fragment was isolated from the gel; about 8 μg of fragment were obtained and suspended in 10 μl of TE buffer.

Approximately 10 μg of plasmid pSV2-β-globin DNA (NRRL B-15928) were dissolved in 10 μl of 10X HindIII reaction buffer, 5 μl (~50 units) of restriction enzyme HindIII, and 85 μl of H₂O, and the reaction was placed at 37° C. for 2 hours. The reaction mixture was then made 0.25M in NaOAc, and after the addition of two volumes of ethanol and incubation in a dry ice-ethanol bath, the DNA was pelleted by centrifugation. The HindIII-digested plasmid pSV2-β-globin was dissolved in 10 μl of 10X BglII buffer, 5 μl (~50 units) of restriction enzyme BglII, and 85 μl of H₂O, and the reaction was placed at 37° C. for two hours. After the BglII digestion, the reaction mixture was loaded onto a 1% agarose gel, and the fragments were separated by electrophoresis. The desired ~4.2 kb HindIII-BglII restriction fragment was isolated from the gel; about 5 μg of the desired fragment were obtained and suspended in 10 μl of TE buffer.

Two μl of the ~0.29 kb HindIII-SalI fragment of plasmid pSV2-HPC8, 2 μl of the ~1.15 kb SalI-BglII fragment of plasmid pSV2-HPC8, and 2 μl of the ~4.2 kb HindIII-BglII fragment of plasmid pSV2-β-globin were mixed together and ligated with T4 DNA ligase. The ligated DNA constituted the desired plasmid pL133; a restriction site and function map of plasmid pL133 is presented in FIG. 2 of the accompanying drawings. The ligated DNA was used to transform *E. coli* K12 RR1, and the desired *E. coli* K12 RR1/pL133 transformants were identified by their ampicillin-resistant phenotype and by restriction enzyme analysis of their plasmid DNA.

F. Construction of Plasmid pLPC From Plasmids pL133 and pBLcat

About 20 μg of plasmid pBLcat DNA were dissolved in 10 μl of 10X HindIII buffer and 80 μl of H₂O. About 10 μl (~100 units) of restriction enzyme HindIII were added to the solution of plasmid pBLcat DNA, and the resulting reaction was incubated at 37° C. for 2 hours. The HindIII-digested plasmid pBLcat DNA was loaded onto an agarose gel and electrophoresed until the ~0.87 kb HindIII restriction fragment that comprises the BK enhancer and Ad2 late promoter was separated from the other digestion products; then, the ~0.87 kb fragment was isolated, purified, and prepared for ligation. About 2 μg of the desired fragment were obtained and dissolved in 5 μl of TE buffer.

About 1.5 μg of plasmid pL133 DNA were dissolved in 2 μl of 10X HindIII buffer and 16 μl of H₂O. About 1 μl (~10 units) of restriction enzyme HindIII was added to the solution of DNA, and the resulting reaction was incubated at 37° C. for 2 hours. The DNA was then diluted to 100 μl with TE buffer and treated with ~0.06 units of calf-intestinal alkaline phosphatase, and the resulting reaction was incubated at 37° C. for 30 minutes. The solution was adjusted to contain 1X SET (5 mM Tris-HCl, pH=7.8; 5 mM EDTA; and 150 mM NaCl), 0.3M NaOAc, and 0.5% SDS and then incubated at 65° C. for 45 minutes. The HindIII-digested plasmid pL133 DNA was then extracted twice with phenol and once with chloroform, precipitated with ethanol, and resuspended in 10 μl of TE buffer.

About 5 μl of the ~0.87 kb HindIII restriction fragment of plasmid pBLcat were added to the 1.5 μg (10 μl) of HindIII-digested plasmid pL133, and then, 2 μl of 10X ligase buffer, 1 μl (~10 units) of T4 DNA ligase, and 2 μl of H₂O were added to the solution of DNA, and the resulting reaction was incubated at 16° C. overnight. The ligated DNA constituted the desired plasmid pLPC.

The ligated DNA was used to transform *E. coli* K12 HB101 in substantial accordance with the procedure of Example 2B. The transformed cells were plated on L-agar plates containing ampicillin, and the plasmid DNA of the ampicillin-resistant transformants was examined by restriction enzyme analysis to identify the *E. coli* K12 HB101/pLPC transformants. The ~0.87 kb HindIII restriction fragment that encodes the BK enhancer and Ad2 late promoter could insert into HindIII-digested plasmid pL133 in one of two orientations, only one of which yields plasmid pLPC. A restriction site and function map of plasmid pLPC is presented in FIG. 1, Part D, of the accompanying drawings.

EXAMPLE 3

The Construction of Plasmid pLPC-167G

Plasmid pLPC-167G was constructed in substantial accordance with the site-specific mutagenesis and other construction protocols used in the construction of plasmid pLAPC, as described in Example 1. Buffers and annealing conditions used in the construction of plasmid pLPC-167G, however, were as described by Zoller and Smith, 1984, DNA 3:479-489.

In the construction of plasmid pLPC-167G, phage M13mp18-HE1 (see Example 1B) were subjected to site-specific mutagenesis using the mutagenizing oligonucleotide depicted below:

5'-GACCAAGAAGACCAAG-
TAGGCCCGCGGCTCATTGATG-3'.

The mutagenized phage resulting from the site-specific mutagenesis were designated M13mp18-HE4.

Final construction of plasmid pLPC-167G proceeded in a manner analogous to the construction of plasmid pLAPC, set forth in Example 1C. However, plasmid pLAPC was constructed using two restriction fragments originating from plasmid pLPC. In the construction of plasmid pLPC-167G, these same two fragments were instead obtained from plasmid pLAPC. The reason for using plasmid pLAPC as the source of the fragments, instead of plasmid pLPC, was to facilitate restriction analysis in identifying the plasmid pLPC-167G transformants. Because plasmids pLPC and pLPC-167G are very close to the same size, it would have been difficult to distinguish "parentals" (plasmid pLPC) from plasmid pLPC-167G. These parentals could be present, despite the purification of the fragments used in the ligation, due to a variety of factors. However, because plasmid pLAPC is smaller than plasmid pLPC-167G, by obtaining the two fragments from plasmid pLAPC, one could readily distinguish parentals (plasmid pLAPC) from the desired plasmid pLPC-167G. Thus, to construct plasmid pLPC-167G, the ~0.7 kb SstI-SalI restriction fragment of phage M13mp18-HE4 was ligated to the ~3.76 kb EcoRI-SalI restriction fragment of plasmid pLAPC and the ~2.0 kb EcoRI-SstI restriction fragment of plasmid pLAPC. The ligated DNA constituted the desired plasmid pLPC-167G, which was transformed into *E. coli* K12 RV308. The resulting *E. coli* K12 RV308/pLPC-167G transformants were used to obtain a large-scale preparation of plasmid pLPC-167G DNA for use in transformations of eukaryotic cells.

EXAMPLE 4

The Construction of Plasmid pLPC-167F

Plasmid pLPC-167F was constructed in substantial accordance with the site-specific mutagenesis and other construction protocols used in the construction of plasmid pLAPC, as described in Example 1. Buffers and annealing conditions used in the construction of plasmid pLPC-167F, however, were as described by Zoller and Smith, 1984, DNA 3:479-489.

In the construction of plasmid pLPC-167F, phage M13mp18-HE1 (see Example 1B) were subjected to site-specific mutagenesis using the mutagenizing oligonucleotide depicted below:

5'-GACCAAGAAGACCAAG-
TATTCCCGCGGCTCATTGATG-3'.

The mutagenized phage resulting from the site-specific mutagenesis were designated M13mp18-HE5.

Final construction of plasmid pLPC-167F proceeded in a manner analogous to the construction of plasmid pLAPC, set forth in Example 1C. However, plasmid pLAPC was constructed using two restriction fragments originating from plasmid pLPC. In the construction of plasmid pLAPC-167F, these same two fragments were instead obtained from plasmid pLAPC. The reason for using plasmid pLAPC as the source of the fragments, instead of plasmid pLPC, was to facilitate restriction analysis in identifying the plasmid pLPC-167F transformants. Because plasmids pLPC and pLPC-167F are very close to the same size, it would have been difficult to distinguish "parentals" (plasmid pLPC) from plasmid pLPC-167F. However, because plasmid pLAPC is smaller than plasmid pLPC-167F, by obtaining the two fragments from plasmid pLAPC, one could readily distinguish parentals (plasmid pLAPC) from the desired plasmid pLPC-167F. Thus, to construct plasmid pLPC-167F, the ~0.7 kb SstI-SalI restriction fragment of phage M13mp18-HE5 was ligated to the ~3.76 kb EcoRI-SalI restriction fragment of plasmid pLAPC and the ~2.0 kb EcoRI-SstI restriction fragment of plasmid pLAPC. The ligated DNA constituted the desired plasmid pLPC-167F, which was transformed into *E. coli* K12 RV308. The resulting *E. coli* K12 RV308/pLPC-167F transformants were used to obtain a large-scale preparation of plasmid pLPC-167F DNA for use in transformations of eukaryotic cells.

EXAMPLE 5

Construction of Adenovirus-transformed Human Embryonic Kidney Cell Line 293 and Adenovirus-transformed Syrian Hamster Cell Line AV12 Transformants Using Plasmids pLPC-167G and pLPC-167F Human Embryonic Kidney Cell Line 293 is available from the American Type Culture Collection under the accession number ATCC CRL 1573. The adenovirus-transformed Syrian hamster cell line AV12 is also available from the American Type Culture Collection under the accession number ATCC CRL 9595. The transformation procedure described below refers to 293 cells as the host cell line; however, the procedure is generally applicable to most eukaryotic cell lines, including the AV12 cell line, and to the expression vectors of the invention.

293 cells are obtained from the ATCC under the accession number CRL 1573 in a 25 mm² flask containing a confluent monolayer of about $5.5 \times 10^6$ cells in Eagle's Minimum Essential Medium (Gibco) with 10% heat-inactivated horse serum. The flask is incubated at 37° C.; medium is changed twice weekly. Media is composed of DMEM (Gibco) supplemented with 10% fetal calf serum, 50 μg/ml gentamicin, and 10 μg/ml AquaMEPHYTON® phytonadione vitamin $K_1$ (Merck Sharp and Dohme, Merck and Co., Inc., West Point, Pa. 19486). The cells are subcultured by removing the medium, rinsing with Hank's Balanced Salts solution (Gibco), adding 0.25% trypsin (containing 0.2 g/L EDTA) for 1-2 minutes, rinsing with fresh medium, aspirating, and dispensing into new flasks at a subcultivation ratio of 1:5 or 1:10.

One day prior to transformation, cells are seeded at $0.7 \times 10^6$ cells per 100 mm dish. Sterile, ethanol-precipitated plasmid DNA dissolved in TE buffer is used to prepare a 2X DNA-CaCl₂ solution containing 25 μg/ml of the transforming plasmid DNA (for plasmid pLPC-167F or pLPC-167G transformations, usually two plasmids are used, plasmid pLPC-167F or pLPC-167G and a plasmid that contains a selectable marker, as discussed below) and 250 mM CaCl₂. 2X HBSS is prepared containing 280 mM NaCl, 50 mM Hepes, and 1.5 mM sodium phosphate, with the pH adjusted to 7.05-7.15. The 2X DNA-CaCl₂ solution is added dropwise to an equal volume of sterile 2X HBSS. A one ml sterile plastic pipette with a cotton plug is inserted into the mixing tube that contains the 2X HBSS, and bubbles are introduced by blowing while the DNA is being added. The calcium-phosphate-DNA precipitate is allowed to form without agitation for 30-45 minutes at room temperature.

The precipitate is then mixed by gentle pipetting with a plastic pipette, and one ml (per plate) of precipitate is added directly to the 10 ml of growth medium that covers the recipient cells. After 4 hours of incubation at 37° C., the media is replaced with fresh media and the cells allowed to incubate for an additional 72 hours before providing selective pressure. For plasmids that do not comprise a selectable marker that functions in eukaryotic cells, such as either plasmid pLPC-167F or pLPC-167G, the transformation procedure utilizes a mixture of plasmids: the expression vector of the present invention that lacks a selectable marker; and an expression vector that comprises a selectable marker that functions in eukaryotic cells. A variety of vectors are available for use in such cotransformation systems and include plasmids pSV2-dhfr (ATCC 37146), pSV2-neo (ATCC 37149), pSV2-gpt (ATCC 37145), and pSV2-hyg (NRRL B-18039). Plasmid pSV2-hyg confers resistance to hygromycin B to eukaryotic host cells. This co-transformation technique allows for the selection of cells that contain the plasmid with the selectable marker. These cells are further examined to identify cells that comprise both of the transforming plasmids. Of course, the present invention also comprises expression vectors that contain a selectable marker for eukaryotic cells and thus do not require use of the cotransformation technique.

For cells transfected with plasmids containing the hygromycin resistance-conferring gene, hygromycin B is added to the growth medium to a final concentration of about 200 μg/ml. The cells are then incubated at 37° C. for 2-4 weeks with medium changes at 3 to 4 day intervals. The resulting hygromycin-resistant colonies are transferred to individual culture flasks for characterization. Plasmid pSV2-neo confers resistance to neomycin (G418 is also used in place of neomycin), and selection of G418-resistant colonies is performed in substantial accordance with the selection procedure for hygromycin-resistant cells, except that G418 is added to a final concentration of 400 μg/ml.

The use of the dihydrofolate reductase (dhfr) gene or the methotrexate resistance-conferring derivative of the dhfr gene (dhfr-mtx) as a selectable marker for introducing a gene or plasmid into a dhfr-deficient cell line and the subsequent use of methotrexate to amplify the copy number of the plasmid has been well established in the literature. 293 cells are dhfr positive, so 293 transformants that contain plasmids comprising the dhfr gene are not selected solely on the basis of the dhfr-positive phenotype, which is the ability to grow in media that lacks hypoxanthine and thymine. Cell lines that do lack a functional dhfr gene and are transformed with dhfr-containing plasmids can be selected for on the basis of the dhfr+ phenotype. Although the use of dhfr as a selectable and amplifiable marker in dhfr-producing cells has not been well studied, evidence in the literature would suggest that dhfr can be used as a selectable marker and for gene amplification in dhfr-producing cells. The present invention is not limited by the selectable marker used on expression vectors. Moreover, amplifiable markers such as metallothionein genes, adenosine deaminase genes, or members of the multigene resistance family, exemplified by the P-glycoprotein gene, can be utilized.

Transformation of the 293 and AV12 cell lines with a mixture of plasmid pLPC-167F or pLPC-167G and a hygromycin resistance-conferring vector and subsequent selection for hygromycin-resistant cells yielded a number of transformants. (Other transformants were obtained by using plasmid pSV2-neo as the cotransforming vector and selecting for G418-resistant cells.) These transformants are analyzed, as described in Example 6, to determine which hygromycin-resistant cells contained plasmid pLPC-167F or pLPC-167G.

EXAMPLE 6

Analysis of 293 and AV12 Cell Lines Transformed with a Mixture of Plasmid pLPC-167F or pLPC-167G and a Hygromycin Resistance Conferring Plasmid for the Secretion of Protein C Zymogen The hygromycin-resistant transformants obtained in Example 5 are grown on 100 mm² tissue culture dishes at a density of several hundred cell clones per tissue culture dish. The media is decanted, and the cells are rinsed twice with 5 ml aliquots of Hank's Balanced salt solution (Gibco). A solution of sterile 0.45% agar (Sigma Type 4 agarose, catalogue #A3643, Sigma Chemical Co., P.O. Box 14508, St. Louis, Mo. 63178) is prepared by mixing 1 ml of 1.8% agar (47° C.) with 3 ml of Dulbecco's Modified Eagle's (DME) Salts (Gibco) (37° C.), and 2 ml of this 0.45% agar solution are layered over the cells.

Nitrocellulose filters (Schleicher and Schuell, Inc., Keene, N.H. 03431) are boiled and then autoclaved 2 hours to remove the wetting agent, which is toxic to the cells. The filters are then placed on top of the agar layer, and after air bubbles are removed, the plates are incubated at 37° C. for 1 to 3 hours. The FEBS 191(1):75; Suzuki et al., 1985, J. Biochem. 97:127–138; and EPO Pub. No. 138222. The avidin D and biotinylated horse radish peroxidase (HRP) used in the assay are obtained in a Vectastain ™ kit (Vector Laboratories, Inc., 30 Ingold Road, Burlingame, Calif. 94010). Biotin is also obtained from Vector Laboratories, Inc.

The filters are rinsed four times with PBS at 4° C. Then, avidin D and biotinylated horse radish peroxidase are prepared and added as per the manufacturer's instructions in the Vectastain ™ (Vector Laboratories) kit. The filters are incubated with the HRP-conjugated avidin D for 1 hour at 4° C. (longer incubation times, i.e., overnight, can be used when small amounts of protein are being secreted); then, the filters are rinsed four times with PBS at 4° C.

To develop the indicator color on the filters, about 30 mg of HRP color-development reagent (4-chloro-1-napthol, Sigma) dissolved in ice-cold 100% methanol are added to 50 ml of PBS and 30 μl of 30% $H_2O_2$. This mixture is added to the nitrocellulose filters, which are incubated at room temperature until the color develops. Colonies secreting the most human protein C zymogen of the invention will be indicated on the filters not only by earliest appearance of the color but also by darker spots on the filter.

After the filters have been developed, the filters are again realigned with the original plates to determine which colonies are associated with which spots on the filter. The colonies secreting the most human protein C zymogen of the invention are then selected and used for production of the zymogen. filters, previously marked to indicate the original orientation of the filter on the dish so as to facilitate later identification of colonies, are then removed and placed in PBS (50 mM Tris-HCl, pH=7.2, and 150 mM NaCl).

To keep the cells on the dish viable during analysis of the filters, the cells are overlayed with 8 ml of a mixture containing 2 ml of 1.8% agar (47° C.), 2 ml of DME salts (37° C.), and 4 ml of DME salts with 20% fetal bovine serum (37° C.). The cells are then placed in a 37° C. incubator.

All washes and reactions carried out on the filters are accomplished while the filters are on a rocking platform. The filters are first blocked by incubation at room temperature in 5% milk in PBS. The filters are then rinsed (5 minutes/rinse) four times in PBS. A 10 μg/ml biotinylated goat anti-human protein C polyclonal antibody in 2.5% bovine serum albumin is added to the filter (in sufficient quantities to cover the filter), which is then incubated at 37° C. for 1 hour.

Purification of protein C, for subsequent use to prepare antibody against protein C, can be accomplished as described by Kisiel, 1979, J. Clin. Invest. 64:761. Polyclonal antibody can be prepared by the procedure disclosed in *Structural Concepts in Immunology and Immunochemistry* by E. A. Kabat, published in 1968 by Holt, Rhinehart, and Winston. Monoclonal antibody, which is also suitable for use in the assay, can be prepared as disclosed in Kohler and Milstein, 1975, Nature, 256:495, or as disclosed in U.S. Pat. No. 4,696,895; EPO Pub. No. 205046; Laurell et al., 1985, Those skilled in the art will recognize that the above assay is merely illustrative of the method of identifying high secreting cell lines. A variety of assay procedures can be successfully employed in the method. For instance, a double-antibody reaction can be employed in which the biotinylated goat anti protein C antibody is replaced with a goat anti-protein C antibody (IgG) and a biotinylated anti-goat IgG antibody.

We claim:
1. A DNA compound comprising a coding sequence for a protein, said protein comprising, from the amino terminus to the carboxyterminus:
 a) a signal peptide and propeptide of a γ-carboxylated, secreted protein;
 b) the light chain of human protein C;
 c) a dipeptide selected from the group consisting of lysine-arginine, arginine-lysine, lysine-lysine, and arginine-arginine; and
 d) the amino acid residue sequence:

ASP THR GLU ASP GLN GLU ASP GLN VAL $R_1$ $R_2$ ARG LEU ILE $R_3$ GLY LYS MET THR ARG ARG

GLY ASP SER PRO

TRP GLN VAL VAL LEU LEU ASP SER LYS LYS LYS

LEU ALA CYS GLY ALA

VAL LEU ILE HIS PRO SER TRP VAL LEU THR ALA

ALA HIS CYS MET ASP

GLU SER LYS LYS LEU LEU VAL ARG LEU GLY GLU

TYR ASP LEU ARG ARG

TRP GLU LYS TRP GLU LEU ASP LEU ASP ILE LYS GLU

VAL PHE VAL HIS

PRO ASN TYR SER LYS SER THR THR ASP ASN ASP ILE

ALA LEU LEU HIS

LEU ALA GLN PRO ALA THR LEU SER GLN THR ILE

VAL PRO ILE CYS LEU

PRO ASP SER GLY LEU ALA GLU ARG GLU LEU ASN

GLN ALA GLY GLN GLU

THR LEU VAL THR GLY TRP GLY TYR HIS SER SER

ARG GLU LYS GLU ALA

LYS ARG ASN ARG THR PHE VAL LEU ASN PHE ILE

LYS ILE PRO VAL VAL

PRO HIS ASN GLU CYS SER GLU VAL MET SER ASN

MET VAL SER GLU ASN

MET LEU CYS ALA GLY ILE LEU GLY ASP ARG GLN

ASP ALA CYS GLU GLY

ASP SER GLY GLY PRO MET VAL ALA SER PHE HIS

GLY THR TRP PHE LEU

VAL GLY LEU VAL SER TRP GLY GLU GLY CYS GLY

LEU LEU HIS ASN TYR

GLY VAL TYR THR LYS VAL SER ARG TYR LEU ASP

TRP ILE HIS GLY HIS

ILE ARG ASP LYS GLU ALA PRO GLN LYS SER TRP

ALA PRO—COOH wherein $R_1$ is selected from the group consisting of PHE, GLY, TYR, and TRP, $R_2$ is selected from the group consisting of VAL and PRO, $R_3$ is selected from the group consisting of ASP and ASN, ARG is Arginine, ASN is Asparagine, ASP is Aspartic acid, —COOH is the carboxy terminus, CYS is Cysteine, GLN is Glutamine, GLU is Glutamic Acid, GLY is Glycine, HIS is Histidine, —H₂N is the amino terminus, ILE is Isoleucine, LEU is Leucine, LYS is Lysine, MET is Methionine, PHE is Phenylalanine, PRO is Proline, SER is Serine, THR is Threonine, TRP is Tryptophan, TYR is Tyrosine, and VAL is Valine.

2. The DNA compound of claim 1, wherein said signal peptide and propeptide are the signal peptide and propeptide of nascent human protein C.

3. The DNA compound of claim 2, wherein said dipeptide is lysine-arginine.

4. The DNA compound of claim 3, wherein the polypeptide encoded by said DNA is:

| | | | | | | | | | | | | | | |
|---|---|---|---|---|---|---|---|---|---|---|---|---|---|---|
| H₂N-MET | TRP | GLN | LEU | THR | SER | LEU | LEU | PHE | VAL | ALA | THR | TRP | GLY | ILE |
| SER | GLY | THR | PRO | ALA | PRO | ASP | LEU | VAL | PHE | SER | SER | PHE | GLU | ARG |
| ALA | HIS | GLN | VAL | LEU | ARG | ARG | ILE | ARG | ALA | ASN | SER | PHE | LEU | GLU |
| GLU | LEU | ARG | HIS | SER | SER | GLU | LEU | GLU | CYS | ILE | VAL | GLU | ILE | GLU |
| ASP | PHE | GLU | GLU | ALA | LYS | PHE | GLU | GLN | ASN | VAL | ASP | ASP | THR | CYS |
| ALA | PHE | TRP | SER | LYS | HIS | GLY | VAL | ASP | GLN | GLY | LEU | VAL | LEU | LEU |
| LEU | GLU | HIS | PRO | CYS | ALA | CYS | SER | CYS | LEU | HIS | CYS | THR | CYS | PRO |
| ASP | GLY | ILE | GLY | SER | PHE | ASP | LEU | PHE | GLU | ALA | GLY | LEU | GLU | ILE |
| ARG | PHE | CYS | GLN | ARG | PHE | SER | LEU | GLU | ASP | PRO | TRP | ARG | ASP | GLY |
| GLY | GLY | CYS | THR | HIS | GLY | LEU | LEU | ASP | VAL | THR | LEU | GLN | ARG | ASN |
| SER | CYS | ALA | PRO | GLY | TYR | GLY | GLY | ARG | ASN | ARG | GLU | SER | CYS | CYS |
| PRO | ALA | VAL | LYS | PHE | PRO | ASP | ASP | THR | VAL | GLY | GLN | MET | ASP | VAL |
| LYS | ARG | SER | HIS | LEU | LYS | LYS | LEU | MET | ASP | ALA | ASP | ASP | ARG | HIS |
| R₁ | R₂ | ARG | LEU | ILE | R₃ | SER | VAL | THR | TRP | HIS | ASP | CYS | CYS | VAL |
| TRP | GLN | VAL | VAL | LEU | LEU | GLY | ARG | LYS | ALA | ASP | ARG | LEU | GLY | PRO |
| VAL | LEU | ILE | HIS | PRO | SER | ASP | ILE | THR | LYS | LYS | THR | PHE | MET | ALA |
| GLU | SER | LYS | LYS | GLU | LEU | TRP | LEU | GLY | ALA | TYR | SER | ILE | LYS | ASP |
| TRP | GLU | LYS | TRP | GLU | SER | VAL | LEU | ILE | TYR | GLU | ASP | GLY | PRO | ARG |
| PRO | ASN | TYR | SER | ALA | GLN | ASP | ASP | ASN | LEU | ILE | VAL | LYS | SER | HIS |
| LEU | ALA | GLN | PRO | LEU | ALA | THR | ASP | THR | VAL | ALA | ALA | GLY | CYS | HIS |
| PRO | ASP | SER | GLY | GLY | TRP | ALA | LEU | SER | GLN | PRO | ILE | ALA | TRP | LEU |
| THR | LEU | VAL | THR | THR | PHE | SER | THR | PHE | HIS | ALA | THR | THR | HIS | GLU |
| LYS | ARG | ASN | ARG | CYS | SER | ARG | ARG | ARG | CYS | MET | LEU | LEU | HIS | ALA |
| PRO | HIS | ASN | GLU | GLY | ILE | THR | LEU | SER | GLY | ASP | ILE | ILE | PRO-COOH | VAL |
| MET | LEU | CYS | GLY | PRO | MET | ASP | SER | PHE | HIS | GLY | ALA | CYS | | ASP |
| ASP | SER | GLY | VAL | SER | TRP | SER | ARG | PHE | PRO | LEU | THR | TRP | | GLY |
| VAL | GLY | LEU | VAL | SER | VAL | GLY | GLU | CYS | ALA | GLY | LEU | HIS | | LEU |
| GLY | VAL | TYR | THR | LYS | VAL | ARG | GLN | LEU | ASP | LEU | ILE | HIS | | TYR |
| ILE | ARG | ASP | LYS | GLU | ALA | GLN | ALA | SER | TRP | ALA | | | | HIS | wherein R₁ is PHE, GLY, TYR, or TRP; R₂ is PRO or VAL; and R₃ is ASP or ASN.

5. A recombinant DNA expression vector comprising the DNA compound of claim 4.

| R₁ | R₂ | ARG | LEU | ILE | R₃ | GLY | LYS | MET | THR | ARG | ARG | GLY | ASP | SER | PRO |
|---|---|---|---|---|---|---|---|---|---|---|---|---|---|---|---|
| | | | | | | | ASP | THR | GLU | ASP | GLN | GLU | ASP | GLN | VAL |
| TRP | GLN | VAL | VAL | LEU | LEU | ASP | SER | LYS | LYS | LYS | LEU | ALA | CYS | GLY | ALA |
| VAL | LEU | ILE | HIS | PRO | SER | TRP | VAL | LEU | THR | ALA | ALA | HIS | CYS | MET | ASP |
| GLU | SER | LYS | LYS | LEU | LEU | VAL | ARG | LEU | GLY | GLU | TYR | ASP | LEU | ARG | ARG |
| TRP | GLU | LYS | TRP | GLU | LEU | ASP | LEU | ASP | ILE | LYS | GLU | VAL | PHE | VAL | HIS |
| PRO | ASN | TYR | SER | LYS | SER | THR | THR | ASP | ASN | ASP | ILE | ALA | LEU | LEU | HIS |
| LEU | ALA | GLN | PRO | ALA | THR | LEU | SER | GLN | THR | ILE | VAL | PRO | ILE | CYS | LEU |
| PRO | ASP | SER | GLY | LEU | ALA | GLU | ARG | GLU | LEU | ASN | GLN | ALA | GLY | GLN | GLU |
| THR | LEU | VAL | THR | GLY | TRP | GLY | TYR | HIS | SER | SER | ARG | GLU | LYS | GLU | ALA |
| LYS | ARG | ASN | ARG | THR | PHE | VAL | LEU | ASN | PHE | ILE | LYS | ILE | PRO | VAL | VAL |
| PRO | HIS | ASN | GLU | CYS | SER | GLU | VAL | MET | SER | ASN | MET | VAL | SER | GLU | ASN |
| MET | LEU | CYS | ALA | GLY | ILE | LEU | GLY | ASP | ARG | GLN | ASP | ALA | CYS | GLU | GLY |
| ASP | SER | GLY | GLY | PRO | MET | VAL | ALA | SER | PHE | HIS | GLY | THR | TRP | PHE | LEU |
| VAL | GLY | LEU | VAL | SER | TRP | GLY | GLU | GLY | CYS | GLY | LEU | LEU | HIS | ASN | TYR |
| GLY | VAL | TYR | THR | LYS | VAL | SER | ARG | TYR | LEU | ASP | TRP | ILE | HIS | GLY | HIS |
| ILE | ARG | ASP | LYS | GLU | ALA | PRO | GLN | LYS | SER | TRP | ALA | PRO—COOH | | | |

6. The vector of claim 5, wherein R₁ is PHE, R₂ is PRO, and R₃ is ASP.

7. The vector of claim 6 that is plasmid pLPC-167F.

8. The vector of claim 5, wherein R₁ is GLY, R₂ is PRO, and R₃ is ASP.

9. The vector of claim 8 that is plasmid pLPC-167G.

10. A eukaryotic host cell transformed with a vector of claim 5.

11. The eukaryotic host cell of claim 10 that is 293/pLPC-167F.

12. The eukaryotic host cell of claim 10 that is 293/pLPC-167G.

13. The eukaryotic host cell of claim 10 that is AV12/pLPC-167F.

14. The eukaryotic host cell of claim 10 that is AV12/pLPC-167G.

15. A method for the recombinant expression of a zymogen form of human protein C in a eukaryotic host cell, which comprises (A) transforming a eukaryotic host cell with a recombinant DNA vector, said vector comprising:
(i) a DNA sequence that encodes an amino acid residue sequence, said amino residue sequence comprising, from the amino terminus to the carboxy terminus:
a) a signal peptide and pro-peptide of a γ-carboxylated, secreted protein;
b) the light chain of human protein C;
c) a dipeptide selected from the group consisting of LYS-ARG, ARG-LYS, LYS-LYS, and ARG-ARG; and
d) the amino acid residue sequence:

wherein R₁ is selected from the group consisting of PHE, GLY, TYR, and TRP, R₂ is selected from the group consisting of VAL and PRO, R₃ is selected from the group consisting of ASP and ASN, ARG is Arginine, ASN is Asparagine, ASP is Aspartic acid, —COOH is the carboxy terminus, CYS is Cysteine, GLN is Glutamine, GLU is Glutamic Acid, GLY is Glycine, HIS is Histidine, ILE is Isoleucine, LEU is Leucine, LYS is Lysine, MET is Methionine, PHE is Phenylalanine, PRO is Proline, SER is Serine, THR is Threonine, TRP is Tryptophan, TYR is Tyrosine, and VAL is Valine; and (ii) a promoter positioned to drive expression of said DNA sequence; and (B) culturing said host cell transformed in step (A) under conditions that allow for expression of said DNA sequence.

16. The method of claim 15, wherein said recombinant DNA expression vector is plasmid pLPC-167F.

17. The method of claim 15, wherein said recombinant DNA expression vector is plasmid pLPC-167G.

18. The method of claim 15, wherein said host cell is selected from the group consisting of 293 and AV12 host cells.

19. The method of claim 18, wherein said host cell cultured in step (B) is selected from the group consisting of 293/pLPC-167F, 293/pLPC-167G, AV12/pLPC-167F, and AV12/pLPC-167G host cells.

20. A vector selected from the group consisting of vectors M13mp18HE4 and M13mp18HE5.

* * * * *

UNITED STATES PATENT AND TRADEMARK OFFICE
CERTIFICATE OF CORRECTION

PATENT NO. :  5,196,322
DATED      :  March 23, 1993
INVENTOR(S):  Nils U. Bang, Hartmut Ehrlich, Brian W. Grinnell, S. Betty Yan It is certified that error appears in the above-indentified patent and that said Letters Patent is hereby corrected as shown below:

Column 51, line 18 reads "...LYS GLU VAL PHR VAL HIS..." should read -- ...LYS GLU VAL PHE VAL HIS...--

Signed and Sealed this

Twenty-seventh Day of December, 1994

Attest:

BRUCE LEHMAN

*Attesting Officer*          *Commissioner of Patents and Trademarks*